(12) United States Patent
Krueger et al.

(10) Patent No.: US 12,097,102 B2
(45) Date of Patent: Sep. 24, 2024

(54) PANT-LIKE DISPOSABLE ABSORBENT ARTICLES WITH IMPROVED CHASSIS CONSTRUCTION

(71) Applicant: Kimberly-Clark Worldwide, Inc., Neenah, WI (US)

(72) Inventors: Eric S. Krueger, Omro, WI (US); Jason K. Sieck, Neenah, WI (US); Kenneth J. Wagner, Greenville, WI (US); Donald J. Osentoski, Menasha, WI (US); Jason G. Csida, Appleton, WI (US); Bradley W. Schoon, Oshkosh, WI (US); Ronald A. Hilt, Oshkosh, WI (US); Chadwick I. Romzek, Neenah, WI (US); Justin M. Mueller, Oshkosh, WI (US); Sohyun S. Park, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1000 days.

(21) Appl. No.: 16/965,173

(22) PCT Filed: Jan. 31, 2018

(86) PCT No.: PCT/US2018/016172
§ 371 (c)(1),
(2) Date: Jul. 27, 2020

(87) PCT Pub. No.: WO2019/152008
PCT Pub. Date: Aug. 8, 2019

(65) Prior Publication Data
US 2021/0052439 A1    Feb. 25, 2021

(51) Int. Cl.
*A61F 13/496* (2006.01)
*A61F 13/49* (2006.01)

(52) U.S. Cl.
CPC ...... *A61F 13/496* (2013.01); *A61F 13/49012* (2013.01); *A61F 13/49017* (2013.01);
(Continued)

(58) Field of Classification Search
CPC .......... A61F 13/15747; A61F 13/49001; A61F 13/49007; A61F 13/49009;
(Continued)

(56) References Cited

U.S. PATENT DOCUMENTS 3,881,488 A  5/1975  Delanty et al.
5,562,645 A  10/1996  Tanzer et al.
(Continued)

FOREIGN PATENT DOCUMENTS

CN    1993095 A    7/2007
CN    101010053 A   8/2007
(Continued)

OTHER PUBLICATIONS

Green Diaper Store, "Happy Heinys One Size Pocket Diaper", May 12, 2015, https://web.archive.org/web/20150512013129/http://www.greendiaperstore.com/happy-heinys-one-size-pocket-diaper.html.
(Continued)

*Primary Examiner* — Leslie A Lopez
*Assistant Examiner* — Jihad Dakkak
(74) *Attorney, Agent, or Firm* — KIMBERLY-CLARK WORLDWIDE, INC.

(57) ABSTRACT

One example pant-like garment may comprise a front panel comprising a front garment-side layer, a front body-side layer, and one or more front chassis elastic members disposed between the front garment-side layer and the front body-side layer, and a rear panel comprising a rear garment-side layer, a rear body-side layer, one or more rear chassis elastic members disposed between the rear garment-side layer and the rear body-side layer, and one or more rear (Continued)

panel leg elastic members directly overlapping the one or more rear chassis elastic members in a vertical direction perpendicular to longitudinal and lateral directions. The garment may further comprise an absorbent assembly disposed between the front panel and the rear panel.

13 Claims, 22 Drawing Sheets

(52) U.S. Cl.
CPC ............... *A61F 2013/49022* (2013.01); *A61F 2013/49025* (2013.01)

(58) Field of Classification Search
CPC .......... A61F 13/49011; A61F 13/49012; A61F 13/49017; A61F 13/49061; A61F 13/494; A61F 13/49406; A61F 13/46446; A61F 13/496; A61F 2013/49022; A61F 2013/49025; A61F 2013/51361
See application file for complete search history.

(56) References Cited

U.S. PATENT DOCUMENTS

| | | | |
|---|---|---|---|
| 5,690,627 A | 11/1997 | Clear et al. | |
| 5,843,056 A | 12/1998 | Good et al. | |
| 6,083,212 A | 7/2000 | Kumasaka | |
| 6,138,282 A | 10/2000 | Follese | |
| 6,217,563 B1 | 4/2001 | Van Gompel et al. | |
| 6,367,089 B2 | 4/2002 | Van Gompel et al. | |
| 6,369,291 B1 | 4/2002 | Uchimoto et al. | |
| 6,443,940 B1 | 9/2002 | Ashton et al. | |
| 6,478,786 B1 | 11/2002 | Glaug et al. | |
| 6,552,245 B1 | 4/2003 | Roessler et al. | |
| 6,582,414 B1 | 6/2003 | Richardson | |
| 6,755,808 B2 | 6/2004 | Balogh et al. | |
| 6,764,478 B2 | 7/2004 | Ashton et al. | |
| 6,794,024 B1 | 9/2004 | Walton et al. | |
| 7,018,369 B2 | 3/2006 | VanGompel et al. | |
| 7,294,593 B2 | 11/2007 | Morman et al. | |
| 7,407,557 B2 | 8/2008 | Wada et al. | |
| 7,582,348 B2 | 9/2009 | Ando et al. | |
| 7,682,350 B2 | 3/2010 | Langdon et al. | |
| 7,749,211 B2 | 7/2010 | Van Gompel et al. | |
| 7,943,219 B2 | 5/2011 | Krueger | |
| 8,043,274 B2 | 10/2011 | Mlinar et al. | |
| 8,167,861 B2 | 5/2012 | Van Gompel et al. | |
| 8,298,205 B2 | 10/2012 | Norrby et al. | |
| 8,328,780 B2 | 12/2012 | Morman et al. | |
| 8,496,638 B2 | 7/2013 | Lord et al. | |
| 8,679,084 B2 * | 3/2014 | Kurihara | A61F 13/4758 604/385.24 |
| 8,753,466 B2 | 6/2014 | Thorson | |
| 8,993,099 B2 | 3/2015 | Lightcap et al. | |
| 9,028,462 B2 | 5/2015 | Poole et al. | |
| 9,060,903 B2 | 6/2015 | Takeuchi et al. | |
| 9,333,119 B2 | 5/2016 | Zink et al. | |
| 9,346,253 B2 | 5/2016 | Ducauchuis et al. | |
| 9,433,539 B2 | 9/2016 | Veith et al. | |
| 9,475,264 B2 | 10/2016 | Melander | |
| 9,498,393 B2 * | 11/2016 | Fukasawa | A61F 13/49011 |
| 9,533,067 B2 | 1/2017 | Schonbeck et al. | |
| 9,597,236 B2 | 3/2017 | Östlin et al. | |
| 9,724,248 B2 | 8/2017 | Hughes et al. | |
| 2002/0147439 A1 | 10/2002 | Tanaka et al. | |
| 2003/0225384 A1 | 12/2003 | Zenker et al. | |
| 2005/0020991 A1 * | 1/2005 | Van Gompel | A61F 13/493 604/385.01 |
| 2005/0038404 A1 | 2/2005 | Takino et al. | |
| 2005/0124948 A1 | 6/2005 | Morman et al. | |
| 2005/0124961 A1 | 6/2005 | Morman et al. | |
| 2005/0131379 A1 | 6/2005 | Otsubo et al. | |
| 2005/0148975 A1 | 7/2005 | Van Gompel et al. | |
| 2006/0144503 A1 | 7/2006 | Carr | |
| 2006/0149208 A1 | 7/2006 | Carr | |
| 2006/0157188 A1 | 7/2006 | Thorson et al. | |
| 2006/0173436 A1 | 8/2006 | Krautkramer et al. | |
| 2006/0228969 A1 | 10/2006 | Erdman | |
| 2007/0208318 A1 | 9/2007 | Loritz et al. | |
| 2008/0009717 A1 | 1/2008 | Herrmann et al. | |
| 2008/0009817 A1 | 1/2008 | Norrby | |
| 2008/0134487 A1 | 6/2008 | Hartono | |
| 2008/0300565 A1 | 12/2008 | Takahashi et al. | |
| 2009/0326503 A1 | 12/2009 | Lakso et al. | |
| 2010/0059168 A1 | 3/2010 | Endo et al. | |
| 2011/0098668 A1 * | 4/2011 | Thorson | A61F 13/49058 604/385.24 |
| 2012/0083757 A1 | 4/2012 | Takahashi et al. | |
| 2012/0277713 A1 * | 11/2012 | Raycheck | A61F 13/49413 604/385.01 |
| 2012/0323201 A1 | 12/2012 | Bissah et al. | |
| 2012/0323204 A1 * | 12/2012 | Poole | A61F 13/49011 604/385.01 |
| 2013/0046266 A1 | 2/2013 | Kawakami | |
| 2013/0240123 A1 | 9/2013 | Lakso et al. | |
| 2013/0317471 A1 | 11/2013 | Morimoto et al. | |
| 2014/0088542 A1 | 3/2014 | Wilkes et al. | |
| 2014/0288521 A1 | 9/2014 | Wade et al. | |
| 2014/0338822 A1 | 11/2014 | Mukai et al. | |
| 2014/0358107 A1 | 12/2014 | Bader et al. | |
| 2016/0067116 A1 | 3/2016 | Beckman et al. | |
| 2016/0262952 A1 | 9/2016 | Wade et al. | |
| 2016/0331600 A1 | 11/2016 | Polidori et al. | |
| 2017/0035625 A1 | 2/2017 | LaVon et al. | |
| 2017/0079851 A1 | 3/2017 | Greening, II et al. | |
| 2017/0105884 A1 * | 4/2017 | Wade | A61F 13/49011 |
| 2017/0112686 A1 | 4/2017 | Esping Östlin et al. | |
| 2017/0128281 A1 | 5/2017 | Takino et al. | |
| 2017/0135869 A1 | 5/2017 | Moriya et al. | |
| 2017/0135872 A1 | 5/2017 | Moriya et al. | |
| 2017/0216105 A1 | 8/2017 | Bäck et al. | |
| 2019/0274897 A1 * | 9/2019 | Morimoto | A61F 13/49061 |
| 2021/0186766 A1 * | 6/2021 | LaVon | A61F 13/49061 |
| 2022/0142828 A1 | 5/2022 | Tong et al. | |

FOREIGN PATENT DOCUMENTS

| | | |
|---|---|---|
| CN | 101803976 A | 8/2010 |
| CN | 102368990 A | 3/2012 |
| EP | 0214636 A2 | 3/1987 |
| EP | 1027874 A2 | 8/2000 |
| EP | 1818030 A1 | 8/2007 |
| JP | 2006247009 A | 9/2006 |
| JP | 2012228307 A | 11/2012 |
| WO | 9500096 A1 | 1/1995 |
| WO | 04078083 A1 | 9/2004 |
| WO | 08143951 A1 | 11/2008 |
| WO | 13180610 A1 | 12/2013 |
| WO | 2016099363 A1 | 6/2016 |

OTHER PUBLICATIONS

Diaper Hero, "Disposable Diaper History", May 3, 2014, http://diaperhero.com/splintered-crying/.
Fameccanica, "Adult incontinence machines", http://www.fameccanica.com/adultincontinencemachines.
Sanimac, "New Machines Construction", http://www.sanimac.it/SANIMAC-2011-6.pdf.
The Natural Baby Company, "Common Materials Used in Cloth Diapers", http://www.thenaturalbabyco.com/guides/cd-guide/common-materials.html.
Xiamen Yalong Commodity Co., Ltd., http://yalong.cc/products/?type=detail&id=232.
Non-woven industry, "Hygiene Components Suppliers Respond to Change", https://www.nonwovens-industry.com/issues/2016-12/view_features/hygiene-components-suppliers-respond-to-change/.
Third Party Observation.
Third Party Observation—EP ref with markup.

(56) References Cited

OTHER PUBLICATIONS

Third Party Observation—WO ref with markup.

* cited by examiner

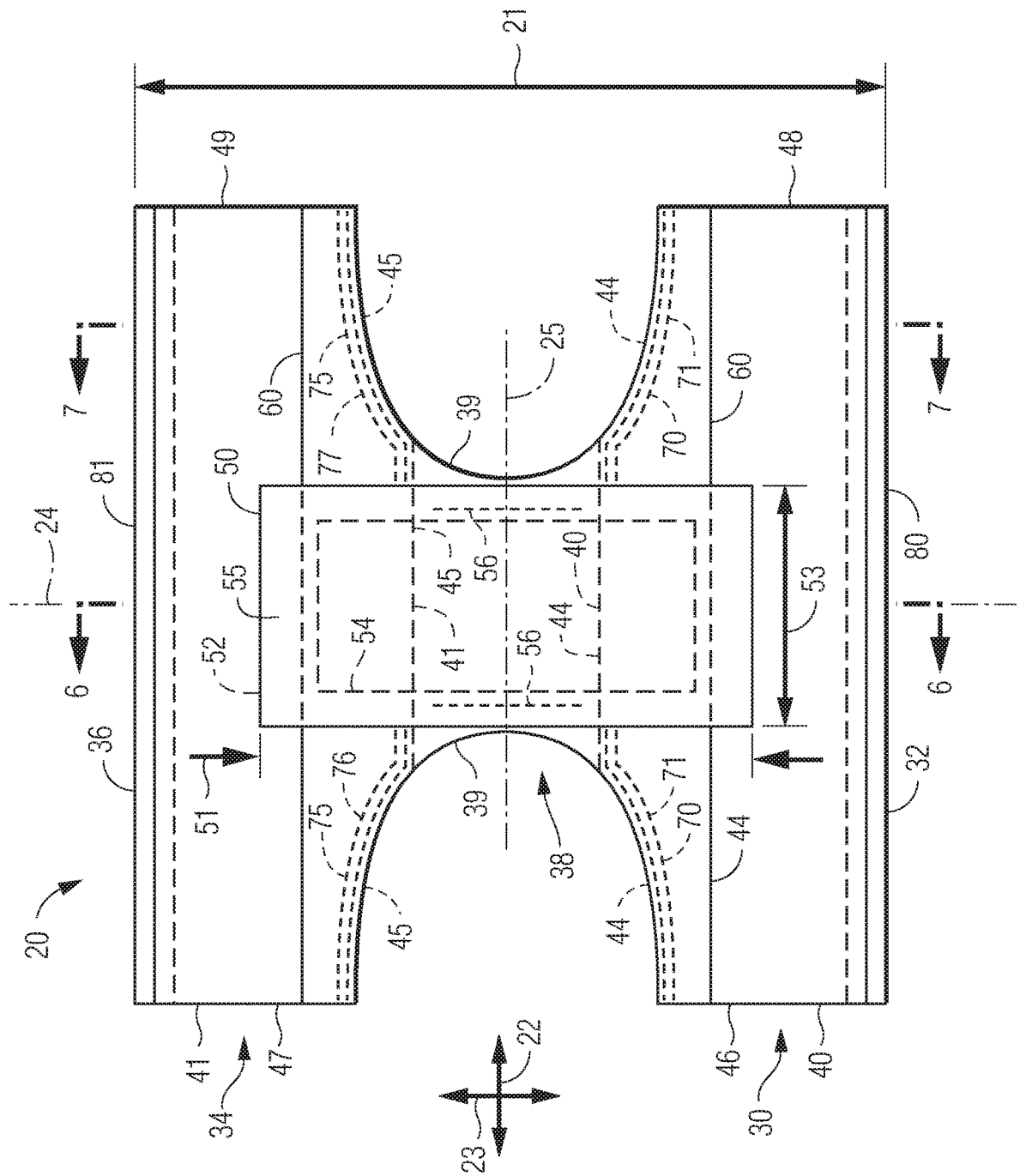

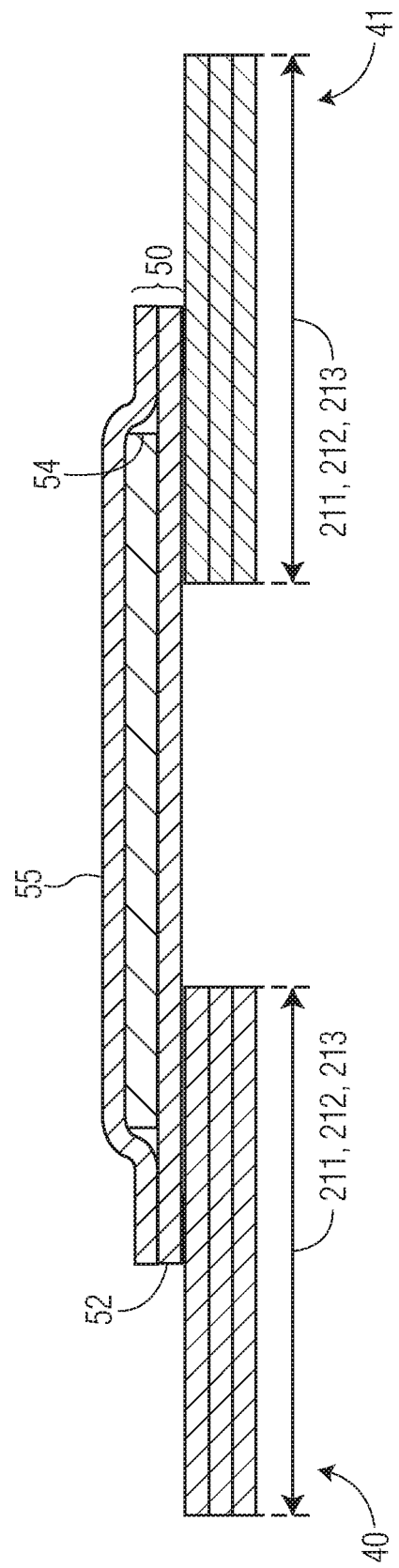

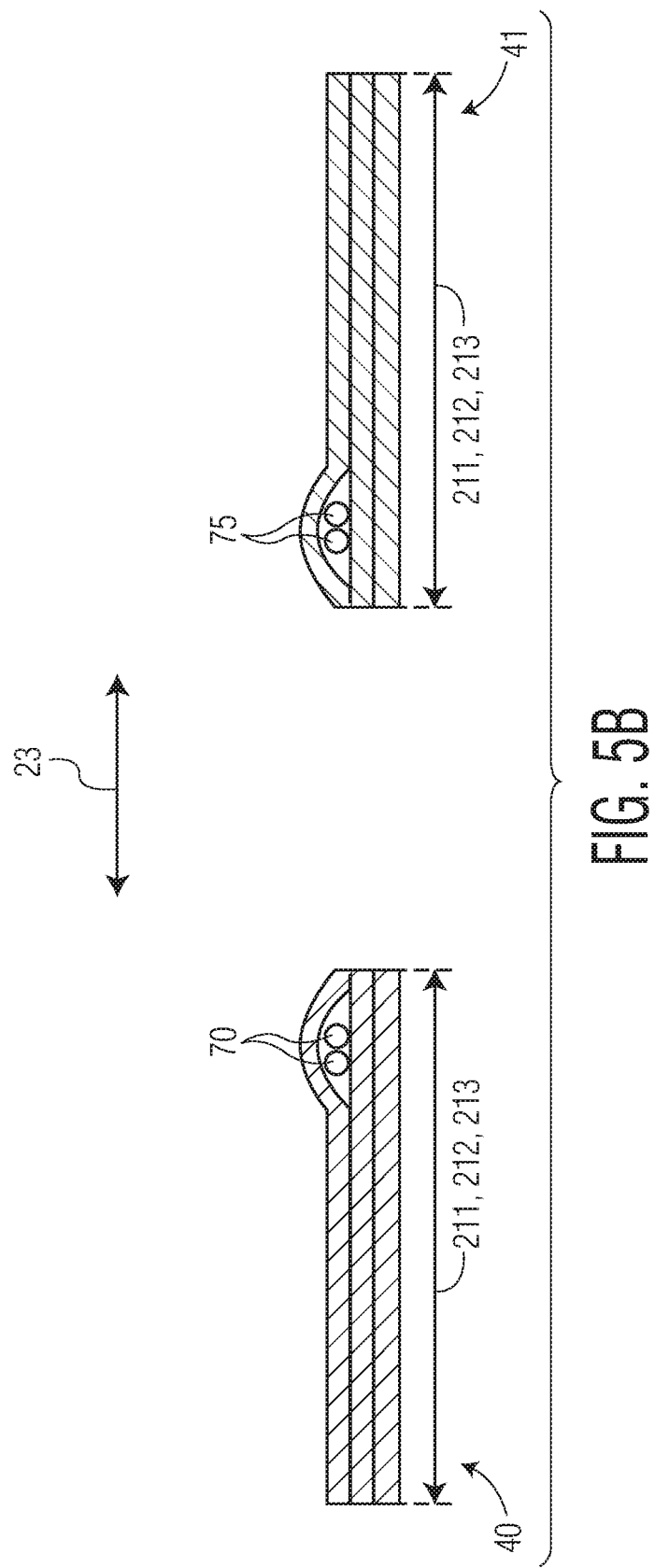

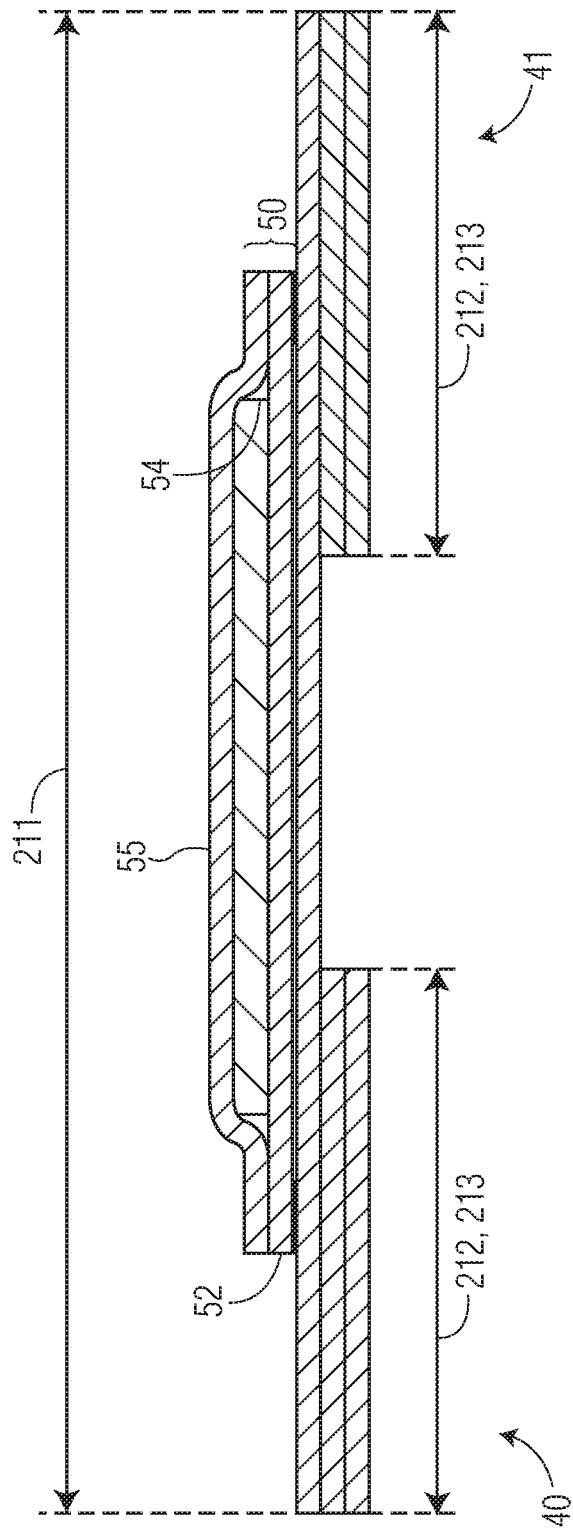

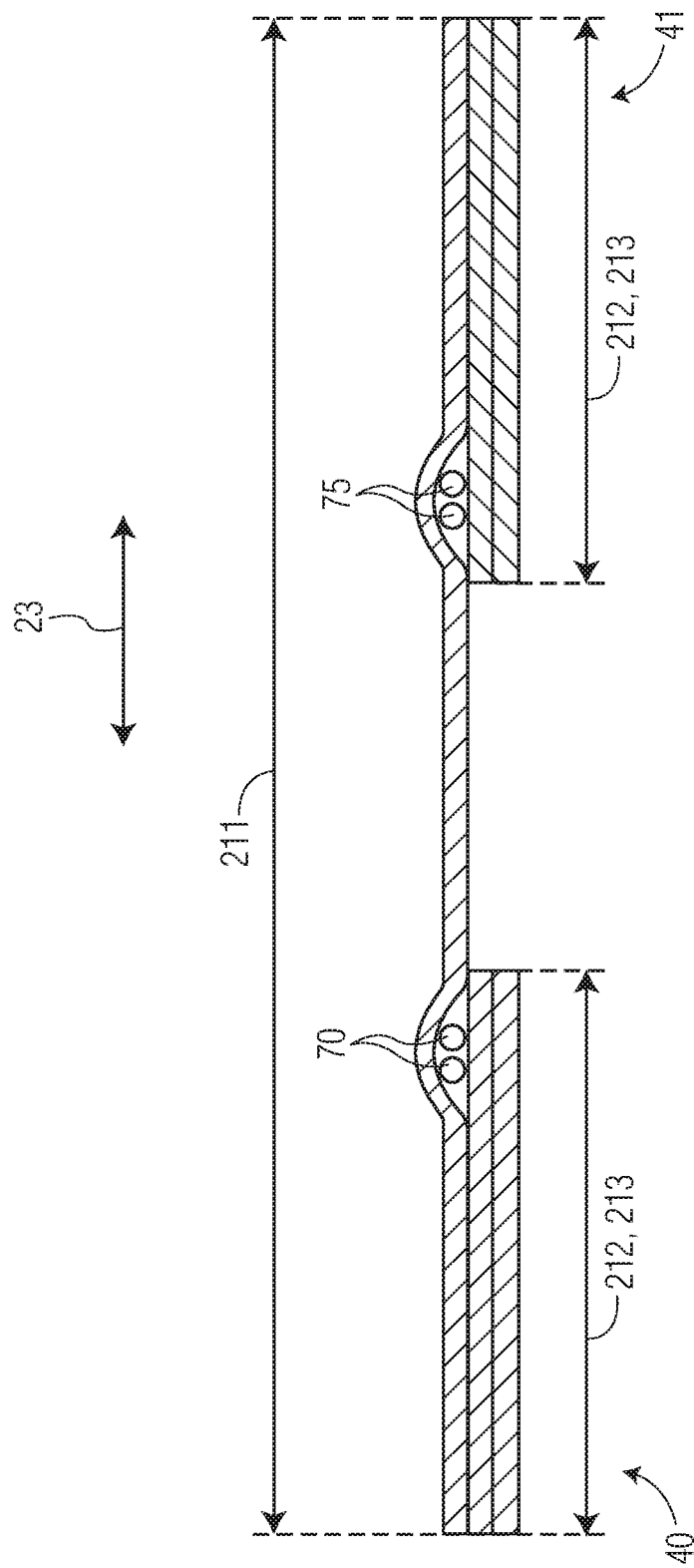

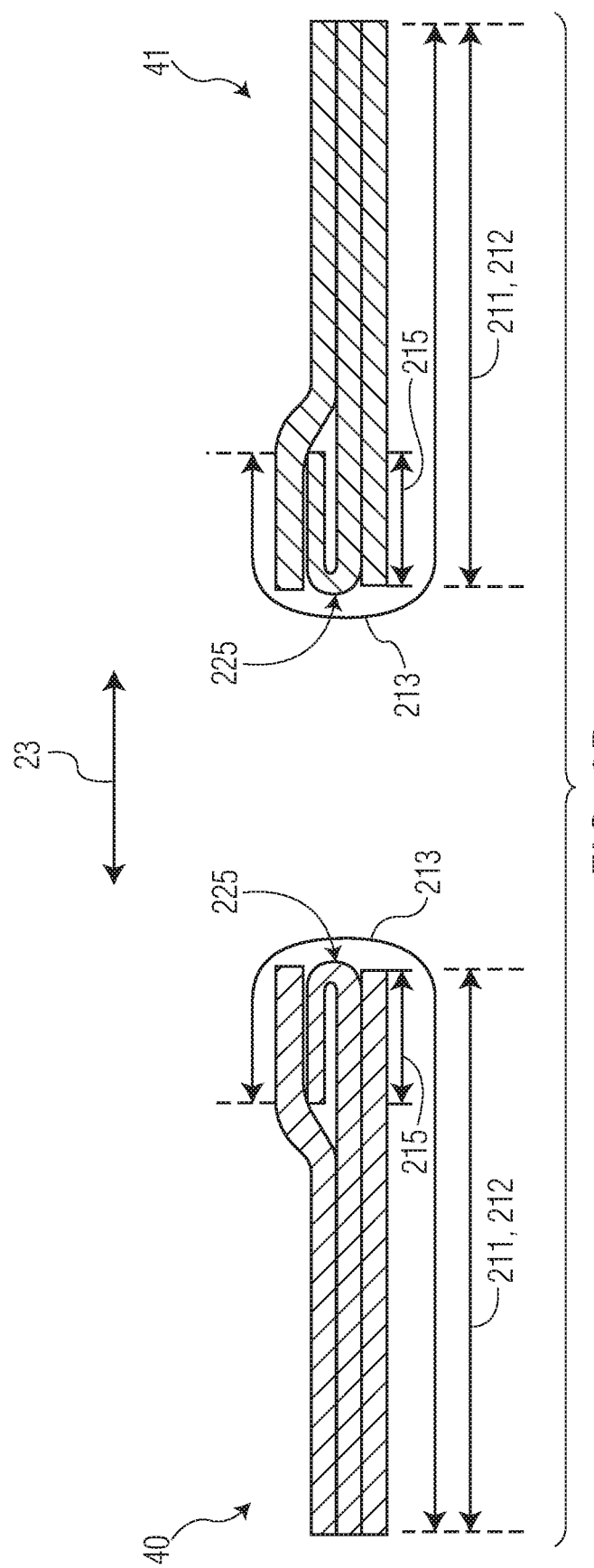

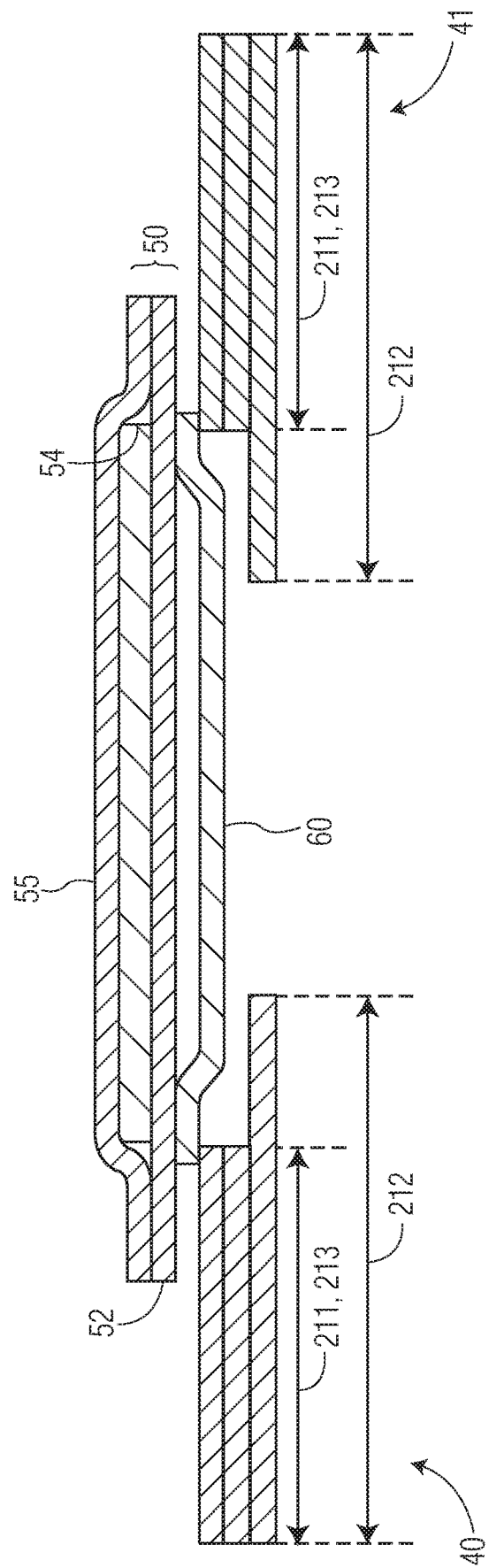

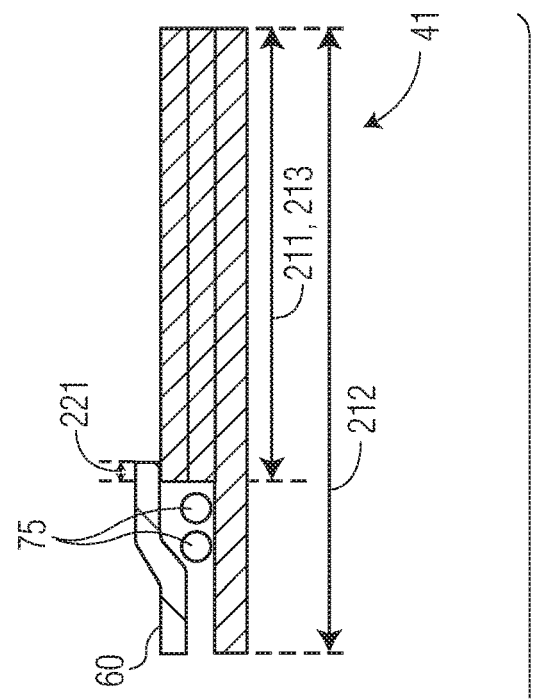
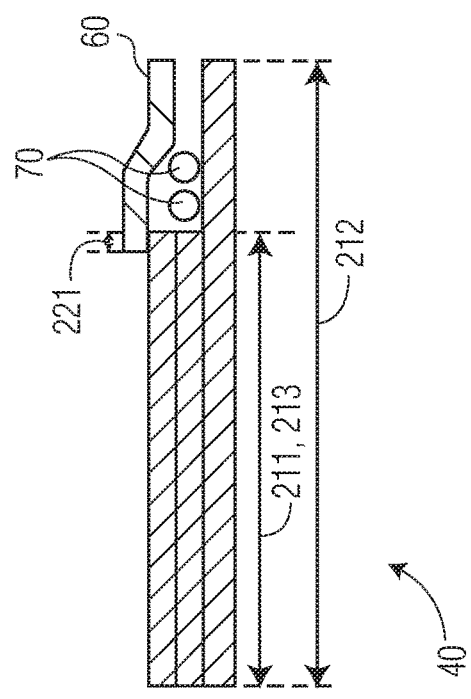
FIG. 9B

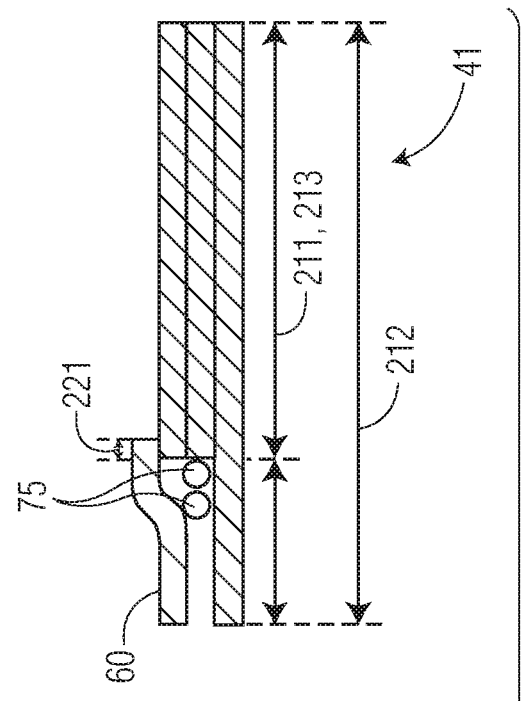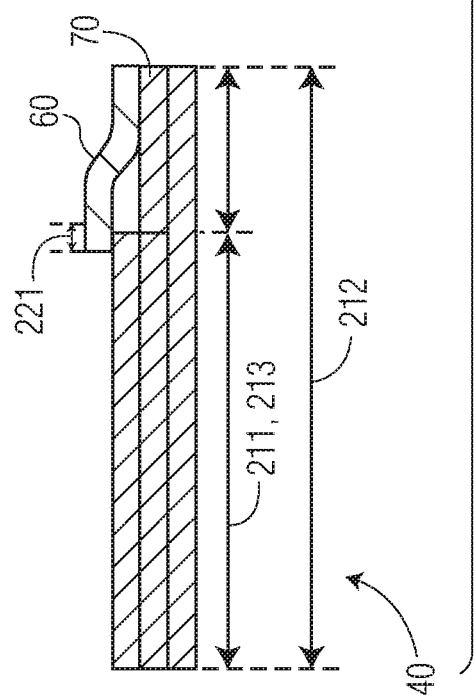
FIG. 10B

PANT-LIKE DISPOSABLE ABSORBENT ARTICLES WITH IMPROVED CHASSIS CONSTRUCTION

TECHNICAL FIELD

The present disclosure is directed to absorbent articles, and more particularly to absorbent articles with an improved chassis structure.

BACKGROUND OF THE DISCLOSURE

People rely on disposable absorbent products in their everyday lives, including such articles as adult incontinence products, enuresis pants, training pants, and diapers. Many manufacturers seek to better meet the needs of users of such products. For example, there is a need to further improve fit, discretion, and leakage protection for many products. With certain products, such as adult incontinence underwear and enuresis pants, it is important that the garment feel as much as possible like "regular" underwear to promote an improved sense of normalcy to the wearer who suffers from incontinence or enuresis. Many conventional pant-like, pull-on style absorbent garments currently on the market employ a product chassis which comprises an elastic material (or materials) sandwiched between two nonwoven fabric layers, with the elastic material providing a secure fit for a wearer while the nonwoven layers provide comfort against the wearer's skin or to the touch.

Some current pant-like absorbent article garments employ pre-laminated elastomeric materials, which comprise a sandwich of an elastomeric film layer disposed between two nonwoven layers, for use as a front and/or rear waist panel. Such materials may be fed into a process whereby additional elastics (such as leg elastics and/or waistband elastics), additional nonwoven materials, and/or an absorbent system are combined with these pre-laminated materials to form a pant-like absorbent article garment. The use of these pre-laminated elastomeric materials can be a drawback in such a processes because the pre-laminated materials do not generally allow for modification of the layers of the laminate. Accordingly, additional and undesired elastics and/or nonwoven layers may then need to be added in order to achieve such goals as improved fit, discretion, and leakage protection.

SUMMARY OF THE DISCLOSURE

The present disclosure is directed to absorbent articles, and more particularly to absorbent articles with an improved chassis structure.

In a first embodiment, a pant-like disposable absorbent garment extending in a longitudinal direction and a lateral direction and having a central longitudinal axis and a central lateral axis, the garment having a front region defining a front waist end edge, a rear region defining a rear waist end edge, and a crotch region longitudinally between the front and rear regions, the crotch region defining two laterally opposed crotch side edges, and the garment defining a garment length extending from the front waist end edge to the rear waist end edge may comprise a front waist panel disposed in the front region comprising: a front panel garment-side facing layer, a front panel body-side facing layer, and one or more front panel chassis elastic members disposed between the front panel garment-side facing layer and the front panel body-side facing layer. The garment may further comprise a rear waist panel disposed in the rear region comprising: a rear panel garment-side facing layer, a rear panel body-side facing layer, one or more rear panel chassis elastic members disposed between the rear panel garment-side facing layer and the rear panel body-side facing layer. The garment may additionally comprise one or more rear panel leg elastic members directly overlapping the one or more rear panel chassis elastic members in a vertical direction perpendicular to longitudinal and lateral directions, and an absorbent assembly disposed between the front panel and the rear panel, the absorbent assembly comprising a topsheet, a backsheet, and an absorbent body disposed between the topsheet and the backsheet.

In a second embodiment, the one or more rear panel leg elastic members of the first embodiment may be disposed adjacent a body-side surface of the one or more rear panel chassis elastic members.

In a third embodiment, the rear panel body-side facing layer of the second embodiment may fully covers the one or more rear panel leg elastic members.

In a fourth embodiment, the rear panel body-side facing layer of the third embodiment may extend between the rear panel and the front panel and forms both the rear panel body-side facing layer and the front panel body-side facing layer.

In a fifth embodiment, the front panel body-side facing layer of any of the third and fourth embodiments may extend between the front panel and the rear panel and forms both the front panel body-side facing layer and the rear panel body-side facing layer.

In a sixth embodiment, the one or more rear panel leg elastic members and at least a portion of the one or more rear panel chassis elastic members of the second embodiment may be uncovered by the rear panel body-side facing layer, and wherein the garment of the second embodiment may further comprise a leg elastic covering panel which covers the one or more rear panel leg elastic members.

In a seventh embodiment, the leg elastic covering panel of the sixth embodiment may further cover at least a portion of the one or more rear panel chassis elastic members which are uncovered by the rear panel body-side facing layer.

In an eighth embodiment, the leg elastic covering panel of any of the sixth and seventh embodiments may overlap the rear panel body-side facing layer by an overlap distance that is greater than 0 mm and less than about 15 mm.

In a ninth embodiment, at least a portion of the one or more front panel chassis elastic members of any of the sixth through eighth embodiments may be uncovered by the front panel body-side facing layer, and the leg elastic covering panel of any of the sixth through eighth embodiments may extend between the rear panel and the front panel and covers at least a portion of the one or more front panel chassis elastic members which are uncovered by the front panel body-side facing layer.

In a tenth embodiment, the one or more front panel chassis elastic members of any of the first through ninth embodiments may comprise a plurality of elastomeric strands, and wherein the one or more rear panel chassis elastic members of any of the first through ninth embodiments may comprise an elastomeric film.

In an eleventh embodiment, the garment of any of the first through tenth embodiments may further comprise one or more front panel leg elastic members, and wherein the one or more front panel leg elastic members comprise an elastomeric film and the one or more rear panel leg elastic members comprise a plurality of elastomeric strands.

In a twelfth embodiment, a pant-like disposable absorbent garment extending in a longitudinal direction and a lateral direction and having a central longitudinal axis and a central lateral axis, the garment having a front region defining a front waist end edge, a rear region defining a rear waist end edge, and a crotch region longitudinally between the front and rear regions, the crotch region defining two laterally opposed crotch side edges, and the garment defining a garment length extending from the front waist end edge to the rear waist end edge may comprise a front waist panel disposed in the front region comprising: a front panel garment-side facing layer, a front panel body-side facing layer, and one or more front panel chassis elastic members disposed between the front panel garment-side facing layer and the front panel body-side facing layer. The garment may further comprise a rear waist panel disposed in the rear region comprising: a rear panel garment-side facing layer, a rear panel body-side facing layer, one or more rear panel chassis elastic members disposed between the rear panel garment-side facing layer and the rear panel body-side facing layer, wherein a portion of the rear panel garment-side facing layer is uncovered by both the rear panel body-side facing layer and the one or more rear panel chassis elastic members. The garment may additionally comprise one or more rear panel leg elastic members disposed adjacent and longitudinally inboard of the one or more rear panel chassis elastic members and directly overlapping, in a vertical direction perpendicular to longitudinal and lateral directions, the uncovered portion of the rear panel garment-side facing layer, a leg elastic covering panel which covers the one or more rear panel leg elastic members, and an absorbent assembly disposed between the front panel and the rear panel, the absorbent assembly comprising a topsheet, a backsheet, and an absorbent body disposed between the topsheet and the backsheet.

In a thirteenth embodiment, the leg elastic covering panel of the twelfth embodiment may overlap the rear panel body-side facing layer by an overlap distance that is greater than 0 mm and less than about 15 mm.

In a fourteenth embodiment, the leg elastic covering panel of any of the twelfth and thirteenth embodiments may extend between the rear panel and the front panel.

In a fifteenth embodiment, the rear panel garment-side facing layer of any of the twelfth through fourteenth embodiments may extend between the rear panel and the front panel and form both the rear panel garment-side facing layer and the front panel garment-side facing layer.

In a sixteenth embodiment, the rear panel garment-side facing layer and the front panel garment-side facing layer of any of the twelfth through fifteenth embodiments may comprise separate materials.

In a seventeenth embodiment, the one or more front panel chassis elastic members of any of the twelfth through sixteenth embodiments may comprise a plurality of elastomeric strands, and wherein the one or more rear panel chassis elastic members of any of the twelfth through sixteenth embodiments may comprise an elastomeric film.

In an eighteenth embodiment, the garment of any of the twelfth through seventeenth embodiments may further comprise one or more front panel leg elastic members, and wherein the one or more front panel leg elastic members comprise an elastomeric film and the one or more rear panel leg elastic members comprise a plurality of elastomeric strands.

In an eighteenth embodiment, a pant-like disposable absorbent garment extending in a longitudinal direction and a lateral direction and having a central longitudinal axis and a central lateral axis, the garment having a front region defining a front waist end edge, a rear region defining a rear waist end edge, and a crotch region longitudinally between the front and rear regions, the crotch region defining two laterally opposed crotch side edges, and the garment defining a garment length extending from the front waist end edge to the rear waist end edge may comprise a front waist panel disposed in the front region comprising: a front panel garment-side facing layer, a front panel body-side facing layer, one or more front panel chassis elastic members disposed between the front panel garment-side facing layer and the front panel body-side facing layer, wherein at least a portion of the one or more front panel chassis elastic members are uncovered by the front panel body-side facing layer, and one or more front panel leg elastic members directly overlapping a body-facing side of the one or more front panel chassis elastic members in a vertical direction perpendicular to longitudinal and lateral directions. The garment may further comprise a rear waist panel disposed in the rear region comprising: a rear panel garment-side facing layer, a rear panel body-side facing layer, one or more rear panel chassis elastic members disposed between the rear panel garment-side facing layer and the rear panel body-side facing layer, wherein at least a portion of the one or more rear panel chassis elastic members are uncovered by the rear panel body-side facing layer, and one or more rear panel leg elastic members directly overlapping a body-facing side of the one or more rear panel chassis elastic members in a vertical direction perpendicular to longitudinal and lateral directions. Additionally, the garment may comprise a leg elastic covering panel extending between the front panel and the rear panel, the leg elastic covering panel: covering the one or more front panel leg elastic members and overlapping the front panel body-side facing layer by an overlap distance that is greater than 0 mm and less than about 15 mm, and covering the one or more rear panel leg elastic members and overlapping the rear panel body-side facing layer by an overlap distance that is greater than 0 mm and less than about 15 mm. Finally, the garment may also comprise an absorbent assembly disposed between the front panel and the rear panel, the absorbent assembly comprising a topsheet, a backsheet, and an absorbent body disposed between the topsheet and the backsheet.

In a twentieth embodiment, the one or more front panel chassis elastic members of the nineteenth embodiment may comprise a plurality of elastomeric strands, and wherein the one or more rear panel chassis elastic members comprise an elastomeric film.

The above summary of some example embodiments is not intended to describe each disclosed embodiment or every implementation of aspects of the disclosure.

BRIEF DESCRIPTION OF DRAWINGS

The aspects of the disclosure may be father understood in consideration of the following detailed description of various embodiments in connection with the accompanying drawings, in which:

FIG. 2 is a plan view of a disposable absorbent garment, according to aspects of the present disclosure, shown in a longitudinally and transversely stretched and laid-flat condition, prior to the joining of the front and back waist regions, and showing the surface of the article that faces toward the wearer when the article is worn;

FIG. 5A is another exemplary cross-section view of the article of FIG. 2 as viewed along the line 6-6;

FIG. 5B is another exemplary cross-section view of the article of FIG. 2 as viewed along the line 7-7;

FIG. 7A is another exemplary cross-section view of the article of FIG. 2 as viewed along the line 6-6;

FIG. 7B is another exemplary cross-section view of the article of FIG. 2 as viewed along the line 7-7;

FIG. 8B is another exemplary cross-section view of the article of FIG. 2 as viewed along the line 7-7;

FIG. 9A is another exemplary cross-section view of the article of FIG. 2 as viewed along the line 6-6;

FIG. 9B is another exemplary cross-section view of the article of FIG. 2 as viewed along the line 7-7;

FIG. 10B is another exemplary cross-section view of the article of FIG. 2 as viewed along the line 7-7;

FIG. 11B is another exemplary cross-section view of the article of FIG. 2 as viewed along the line 7-7;

Figure 1:
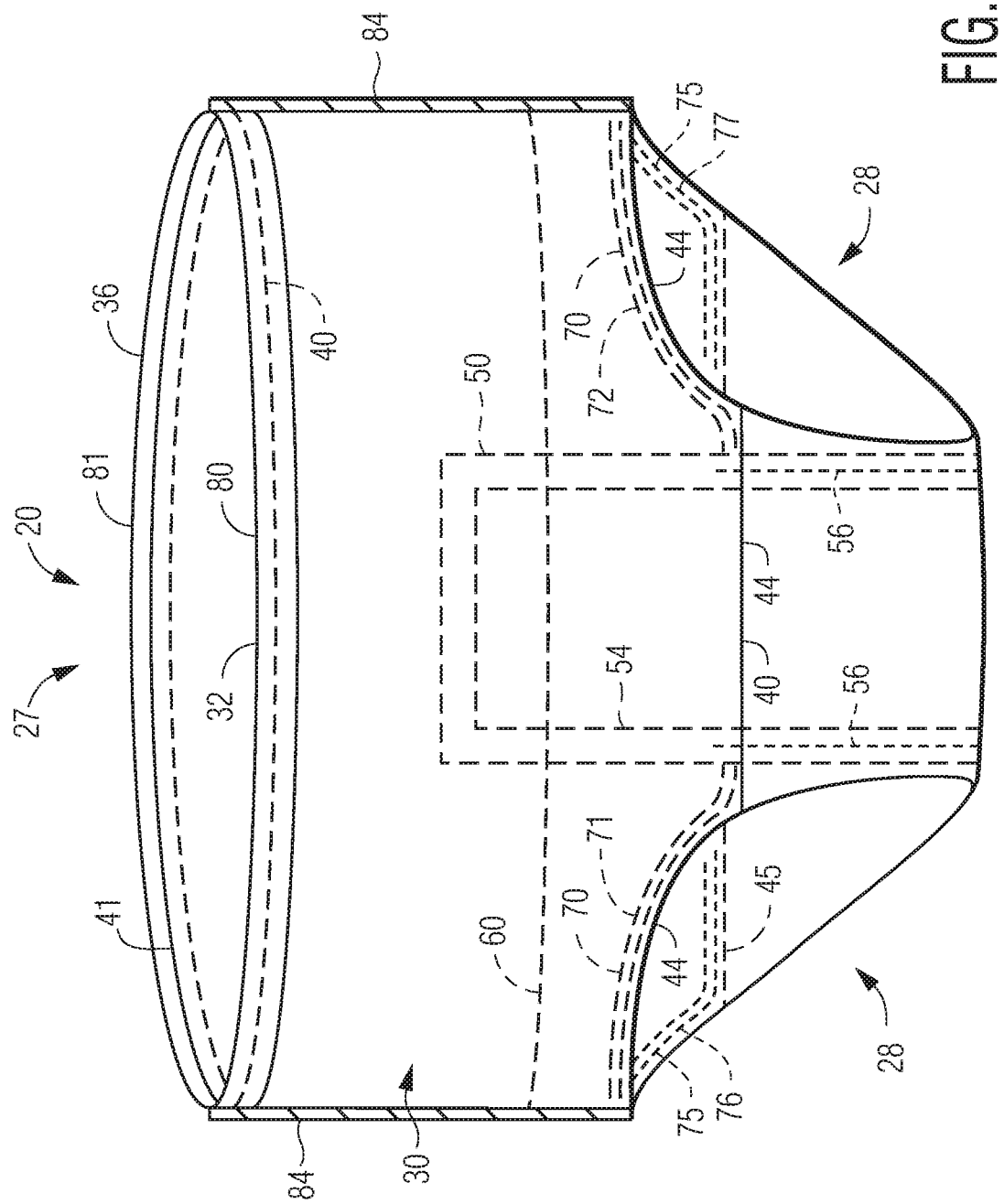
FIG. 1 is a front perspective view of a disposable absorbent garment, according to aspects of the present disclosure.

Repeat use of reference characters in the present specification and drawings is intended to represent the same or analogous features or elements of the disclosure. Additionally, while the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION OF THE DISCLOSURE

Many current pant-like absorbent article garments are formed using pre-laminated elastomeric materials, which generally comprise one or more elastic elements sandwiched between nonwoven layers. Such pre-laminated elastomeric materials come in large rolls, which are then un-rolled into a continuous process for forming pant-like absorbent articles. In such processes, the individual layers of the pre-laminated elastomeric materials may not generally be modified in particular ways which allow for superior chassis construction and reduced manufacturing costs. For example, each of the layers of the pre-laminated elastomeric materials generally have the same dimensions, particularly in the longitudinal direction, and this longitudinal length of each of the layers may be very difficult to change in a continuous process for forming pant-like absorbent articles.

The present disclosure details absorbent article garment structures that may be formed by a continuous process where the laminated elastomeric materials used in the front and rear waist panels (and/or the front and rear waistbands) are formed during the continuous process, as opposed to feeding pre-laminated elastomeric materials into such a process. Forming these laminated elastomeric materials during the process for forming absorbent article garments allows for an improved chassis structure of the pant-like absorbent article garments. For example, forming laminated elastomeric materials during a continuous process for forming absorbent article garments allows for a unique construction of the chassis and/or waistbands by allowing variability in the longitudinal lengths of the materials used to form the elastomeric laminate materials and/or to allow overlapping of multiple elastic elements within a single laminate material. Such chassis and waistband structures will be described herein.

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 20 percent of its elongation. It is generally preferred that the elastomeric material or composite be capable of being elongated by at least 50 percent, more preferably by at least 100 percent, and still more preferably by at least 300 percent of its relaxed length and recover, upon release of an applied force, at least 50 percent of its elongation.

"Integral" is used to refer to various portions of a single unitary element rather than separate structures bonded to or placed with or placed near one another.

"Layer" when used in the singular can have the dual meaning of a single element or a plurality of elements.

"Member" when used in the singular can have the dual meaning of a single element or a plurality of elements.

These terms may be defined with additional language in the remaining portions of the specification.

Referring to FIGS. 1-2, a garment 20 extends along a longitudinal direction 23 and a lateral direction 22 perpendicular to the longitudinal direction 23. As used in describing the various embodiments of the garment 20, according to aspects of the present disclosure, the terms "longitudinal" and "lateral" have their customary meaning, as indicated by the central longitudinal axis 24 and the central lateral axis 25. The central longitudinal axis 24 lies in the plane of the article when the article is in a fully stretched and laid-flat condition, while the front and rear panels are separated, and is generally parallel to a vertical plane that bisects a standing wearer into left and right body halves when the article is worn. The central lateral axis 25 lies in the plane of the article and is generally perpendicular to the central longitudinal axis 24. The garment 20 has a front region 30 defining a front waist end edge 32, a rear region 34 defining a rear waist end edge 36, and a crotch region 38 positioned longitudinally between the front region 30 and the rear region 34. The crotch region 38 defines two laterally opposed crotch side edges 39. The garment 20 defines a garment length 21 that extends from the front waist end edge 32 to the rear waist end edge 36.

The garment 20 includes a front panel 40 which defines a front panel leg edge 44 spaced longitudinally inward from the front waist end edge 32, and first and second laterally opposed front panel side edges 46, 48. The garment 20 also includes a rear panel 41 which defines a rear panel leg edge 45 spaced longitudinally inward from the rear waist end edge 36, and first and second laterally opposed rear panel side edges 47, 49. "Longitudinally inward (or inboard)" as used to describe garment embodiments herein means in a direction longitudinally toward the central lateral axis 25. Likewise, "laterally inward (or inboard)" as used to describe garment embodiments herein means in a direction laterally toward the central longitudinal axis 24. The front panel 40 is longitudinally spaced apart from the rear panel 41. The specific structures of the front and rear panels 40, 41 are described below with respect to FIGS. 3A-11B.

A pair of side seams 84, 84 connects the front region 30 to the rear region 34, such that the garment 20 defines a waist opening 27 and a pair of leg openings 28. The side seams can be permanent but tearable, such as by way of adhesive, thermal, pressure, or ultrasonic bonding, or can be more readily releasable as well as refastenable, such as via the use of mechanical fastening elements.

The garment 20 may further include at least one front leg elastic member 70 disposed adjacent the front panel leg edge 44, and/or at least one rear leg elastic member 75 disposed adjacent the rear panel leg edge 45. Such leg elastic members 70 and/or 75 help to provide additional elastic support around the leg openings 28 to enhance the fit and leakage protection of the garment 20. Each leg elastic member 70, 75 can comprise a single ribbon, strand, or thread (or the like) of elastic material, or each can comprise two, three, or more ribbons, strands, or threads (or the like) of elastic material. Elastic ribbons, strands, threads, and the like suitable for use in disposable absorbent garments are known in the art, one example being LYCRA brand elastic filaments, available from the Dupont Corporation. In particular embodiments, the rear leg elastic member 75 and/or the front leg elastic member 70 extends laterally across the entire garment width. In other embodiments, such as that representatively illustrated in FIGS. 1 and 2, the rear leg elastic member 75 can comprise a pair of rear leg elastic members, such as first and second rear leg elastic members 76, 77 positioned on opposite sides of the absorbent composite 50. Similarly, the front leg elastic member 70 can comprise a pair of front leg elastic members, such as first and second front leg elastic members 71, 72 positioned on opposite sides of the absorbent composite 50. In preferred embodiments, such as that representatively illustrated in FIGS. 1 and 2, each rear leg elastic member 75 can comprise a plurality of elastomeric strands, and/or each front leg elastic member 70 can comprise a plurality of elastomeric strands.

In particular embodiments, an absorbent composite 50 is attached to and between the front panel 40 and the rear panel 41. The absorbent composite 50 comprises a liquid impermeable barrier layer 52 defining a width 53, an absorbent core 54 comprised of liquid-absorbing materials such as cellulosic fluff and/or superabsorbent polymer, a liquid permeable liner 55, and, optionally, crotch elastic members 56. The composite can have a length 51 and a width 53.

FIGS. 3A, 4A, 5A, 6A, 7A, 8A, 9A, 10A, and 11A depict cross-sections of the garment 20 as viewed along line 6-6, while FIGS. 3B, 4B, 5B, 6B, 7B, 8B, 9B, 10B, and 11B depict cross-sections of the garment 20 as viewed along line 7-7. Combined, these FIGS. 3A-11B depict alternative embodiments of chassis structures of garment 20 contemplated by the present disclosure. As can be seen, each of the front and rear panels 40, 41 generally comprise a structure having three layers—a nonwoven body-side facing layer 201, a nonwoven garment-side facing layer 202, and an elastomeric layer 203 disposed between the body-side facing layer 201 and the garment-side facing layer 202, forming an elastomeric laminate material. Generally, the elastomeric layer 203 may comprise one or more chassis elastic members. For example, the elastomeric layer 203 may comprise an elastomeric film, as shown in the FIGS. 3A-11B, while in other contemplated embodiments the elastomeric layer 203 may comprise a plurality of elastomeric strands. In even further embodiments, the elastomeric layer 203 of one of the front panel 40 and the rear panel 41 may comprise an elastomeric film while the other of the front panel 40 and the rear panel 41 may comprise a plurality of elastomeric strands forming a hybrid garment. Accordingly, it should be understood that although the FIGS. 3A-11B depict both the front and rear panels 40, 41 as comprising an elastomeric film for the elastomeric layers 203, this is not required in all contemplated embodiments, and any of the elastomeric layers 203 of any embodiment may comprise a plurality of elastomeric strands instead of an elastomeric film as shown. Many different elastomeric film and strand materials may be suitable for use in garment 20. For instance, any commercially available elastomeric film and/or elastomeric strands may be used in the garment 20. Some exemplary suitable elastomeric materials are described in U.S. Pat. No. 9,549,859, titled "METHOD OE INCORPORATING LEG ELASTICS IN A PANT-LIKE DISPOSABLE ABSORBENT GARMENT, AND GARMENT MADE THEREBY", the entirety of which is hereby incorporated by reference.

Figure 3A:
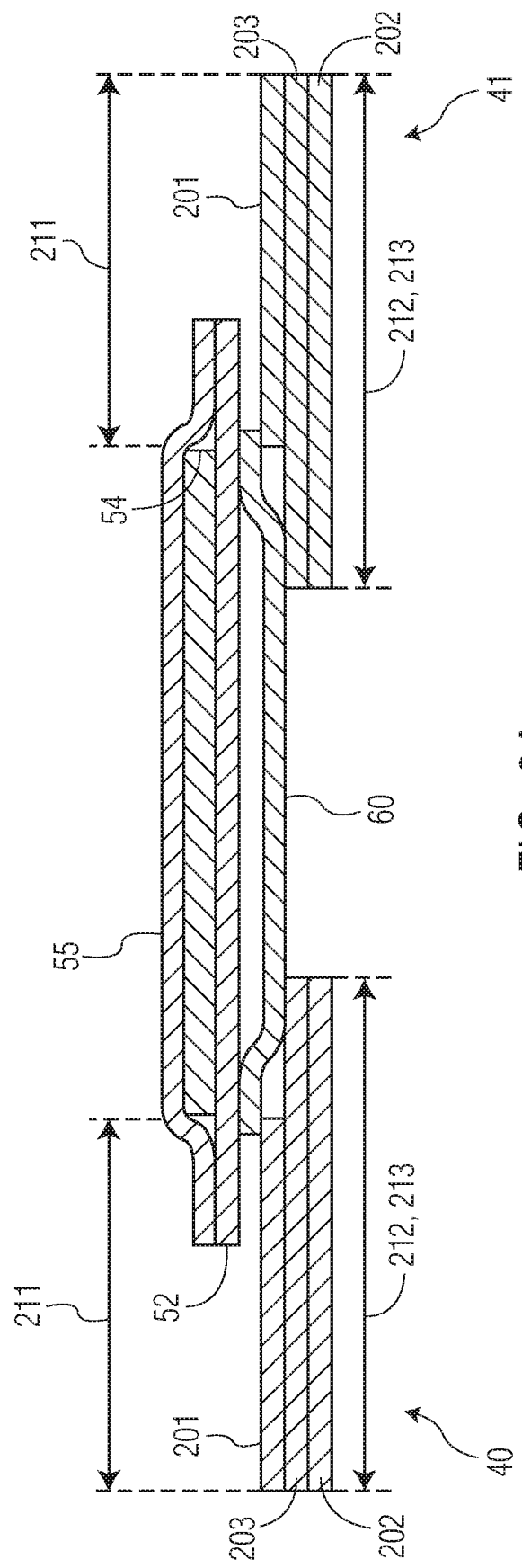
FIG. 3A is one exemplary cross-section view of the article of FIG. 2 as viewed along the line 6-6.
Figure 3B:
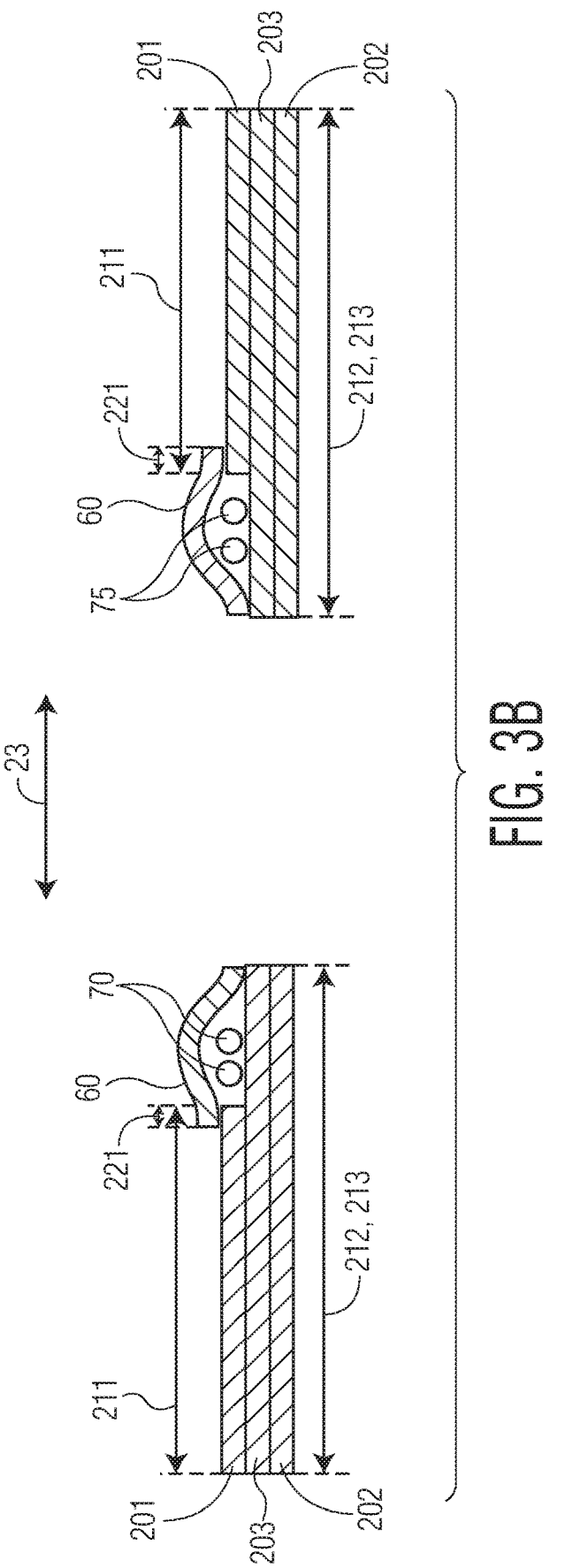
FIG. 3B is one exemplary cross-section view of the article of FIG. 2 as viewed along the line 7-7.

FIGS. 3A and 3B depict one exemplary embodiment of the chassis structure of the garment 20 according to aspects of the present disclosure. As described above, one of the features of the garments 20 is the varying longitudinal lengths of the layers of the elastic laminates which form the front and rear panels 40, 41. For example, each of the layers 201, 202, and 203 of the panels 40, 41 have longitudinal lengths 211, 212, and 213, respectively. Further, in the embodiment of FIGS. 3A and 3B, the longitudinal lengths 211 of the body-side facing layers 201 are less than either of the longitudinal lengths 212 and 213 of the layers 202 and 203, respectively. This leaves a portion of the elastomeric layers 203 uncovered on the body-facing side by the body-side facing layers 201 proximate the central lateral axis 25. As shown in FIG. 3B, this leaves room for placement of leg elastic members 70, 75 adjacent and directly overlapping the body-facing side of the portions of the elastomeric layers 203 that are uncovered by the body-side facing layers 201. This positioning also puts the leg elastic members 70, 75 closer to the central lateral axis 25 than the body-side facing layers 201.

However, in other embodiments, the lengths 211, 212, and 213 may all be the same or the length 211 may even be greater than the lengths 212, 213, but a portion of the layers 203 proximate the central lateral axis 25 may still be uncovered by the layers 201. For instance, the layers 201, 202, and 203 may be shifted relative to each other so that their edges do not align, or body-side facing layers 201 may extend beyond the ends of the garment-side facing layers 202 proximate the waist edges of the garment giving the layers 201 a greater length 211 than the other layers 202, 203. Accordingly, it is not necessary in all embodiments for the length 211 to be less than the lengths 212, 213 to produce a structure whereby a portion of the elastomeric layers 203 are uncovered by the body-side facing layers 201. It should be understood that this relationship is true also for the remaining embodiments and such additional description will be omitted for ease of description.

The garment 20 further includes a leg elastic covering panel 60 spanning between the front panel 40 and the rear panel 41 and connected to the liquid impermeable barrier layer 52 of the absorbent insert 50. The leg elastic covering panel 60 may generally comprise a non-elastomeric nonwoven material, such as a spunbond, a spunbond laminate, a bonded-carded web, or the like, examples of which are known in the art. In at least some embodiments, the leg elastic covering panel 60 may be a soft material and may be at least softer than the liquid impermeable barrier layer 52. In such embodiments, the leg elastic covering panel 60 may act as a portion of the outer cover of the garment 20.

The leg elastic covering panel 60 further covers both the leg elastic members 70, 75 and at least some of the portions of the elastomeric layers 203 that are uncovered by the body-side facing layers 201. The leg elastic covering panel 60 is shown overlapping the body-side facing layers 201 an overlap distance of 221. In some embodiments, the overlap distance 221 may be as small as possible, given manufacturing constraints. In such embodiments, the overlap distance 221 may generally be greater than 0 mm to and less than about less than about 30 mm, or less than about 25 mm, or less than about 20 mm, or less than about 15 mm, or less than about 10 mm, or less than about 5 mm. However, in other embodiments, it may be desired that the leg elastic covering panel 60 has a relatively large overlap distance 221 in order to facilitate incorporation of the leg elastic covering panel 60 into the side seam bonds 84 to strengthen these bonds. In such embodiments, the overlap distance 221 may generally be between about 60 mm and about 90 mm. In this manner, all of the elastic members, e.g. the elastomeric layers 203 of the front and rear panels 40, 41 and the leg elastic members 70, 75, are covered by a nonwoven layer— either the leg elastic covering panel 60, the body-side facing layers 201, or the garment-side facing layers 202.

In other embodiments, however, there may be no overlap between the body-side facing layers 201 and the leg elastic covering panel 60. For example, the leg elastic covering panel may still cover the leg elastic members 70, 75 but there may be a gap having a gap length between the body-side facing layers 201 and the leg elastic covering panel 60. This gap length (not shown) may generally be greater than 0 mm and less than about 10 mm. In such embodiments, then, some part of the elastomeric layers 203 may be uncovered by both of the body-side facing layers 201 and the leg elastic covering panel 60. However, the absorbent insert 50 may be placed over both of the body-side facing layers 201 and the leg elastic covering panel 60 such that the absorbent insert 50 covers such parts of the elastomeric layers 203 that are uncovered by both of the body-side facing layers 201 and the leg elastic covering panel 60.

In the embodiment of FIGS. 3A and 3B, by forming the laminate materials comprising the layers 201, 202, and 203 during the process of forming the garment 20 and varying the longitudinal lengths 211, 212, and 213 of the layers 201, 202, 203, the body-side facing layers 201 may comprise less material than a garment 20 would have in a similar process but which uses pre-laminated materials for the front and rear panels 40, 41. For example, in embodiments where pre-laminated materials are used, the leg elastic members 70, 75 would need to be positioned on top of the body-side facing layer 201. The leg elastic covering panel 60 would then cover both the leg elastic members 70, 75 and the body-side facing layers 201. These portions of the body-side facing layers 201 which the leg elastic covering panel 60 overlaps is unneeded material and represents an increased cost in the manufacture of the garment 20. Accordingly, the chassis construction described in some of the embodiments above allows for minimal-to-no overlap of the leg elastic covering panel 60 with the body-side facing layers 201, resulting in lower manufacturing costs for manufacturing garment 20.

Figure 4A:
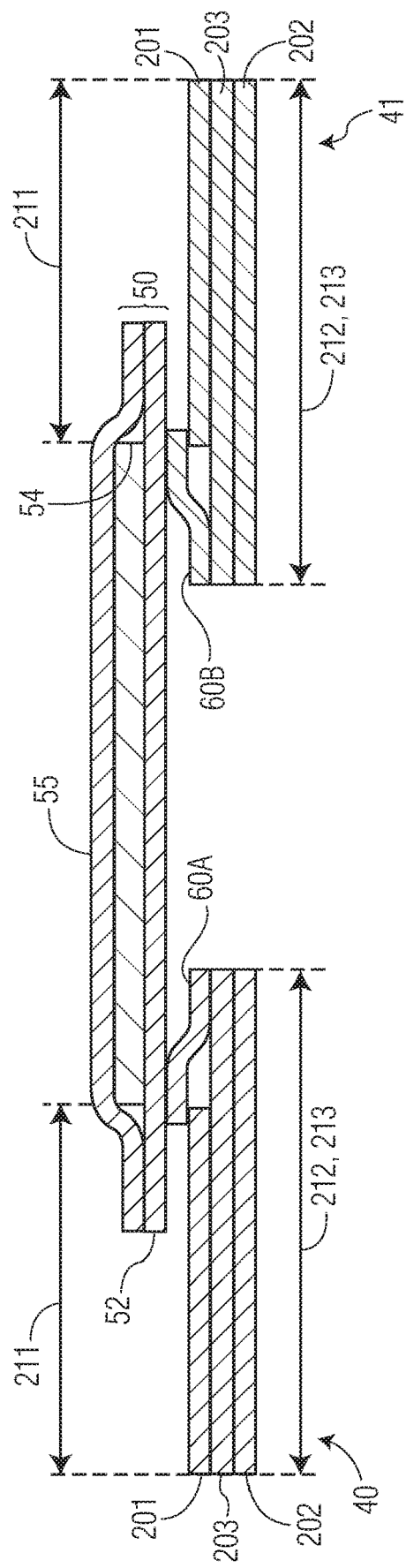
FIG. 4A is another exemplary cross-section view of the article of FIG. 2 as viewed along the line 6-6.
Figure 4B:
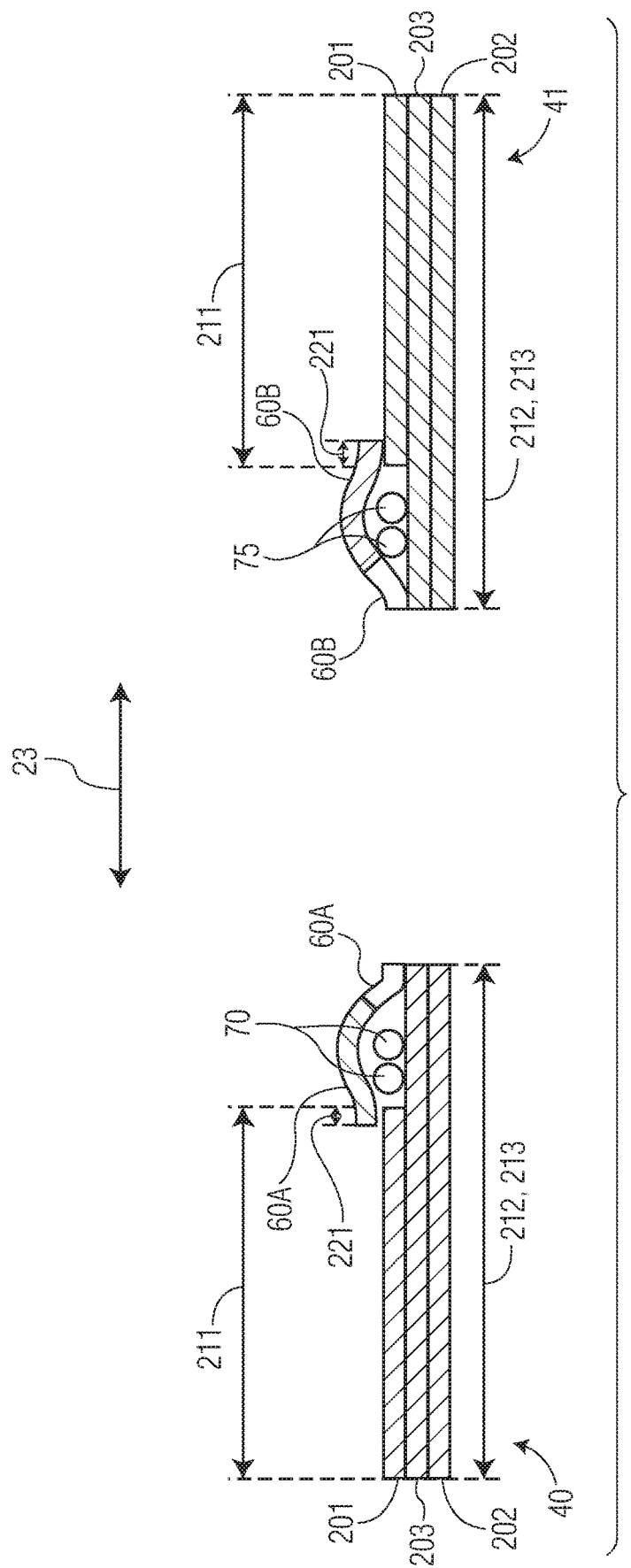
FIG. 4B is another exemplary cross-section view of the article of FIG. 2 as viewed along the line 7-7.

FIGS. 4A and 4B depict another exemplary embodiment of the chassis structure of the garment 20 according to aspects of the present disclosure. In this embodiment, again, the longitudinal lengths 211 of the body-side facing layers 201 are less than either of the longitudinal lengths 212 and 213 of the layers 202 and 203, respectively, leaving a portion of the elastomeric layers 203 uncovered on their body-facing side by the body-side facing layers 201. However, unlike the embodiment of FIGS. 3A and 3B, the embodiment of FIGS. 4A and 4B includes two leg elastic covering panels 60A and 60B. In such an embodiment, the leg elastic covering panels 60A and 60B may not extend between the panels 40, 41. Rather, each of the leg elastic covering panels 60A and 60B may be disposed in only one of the panels 40, 41. The smaller longitudinal lengths 211 of the body-side facing layers 201 results in a portion of the elastomeric layers 203 being uncovered by the body-side facing layers 201 in both of the front and rear panels 40, 41. This structure allows for placement of the leg elastic members 70, 75 adjacent and directly overlapping the body-facing side of the portions of the elastomeric layers 203 that are uncovered by the body-side facing layers 201. This positioning also puts the leg elastic members 70, 75 closer to the central lateral axis 25 than the body-side facing layers 201.

The leg elastic covering panels 60A and 60B are positioned to cover both the leg elastic members 70, 75 and at least part of the uncovered portion of the elastomeric layers 203 of the panels 40, 41. Like with the embodiment of FIGS. 3A and 3B, the leg elastic covering panels 60A and 60B may overlap the body-side facing layers 201 of the front and rear panels 40, 41 by an overlap distance 221. Although, like in the embodiment of FIGS. 3A and 3B, in some examples there may be no overlap between the leg elastic covering panels 60A and 60B and the body-side facing layers 201. Instead, there may be a gap having a gap length between the leg elastic covering panels 60A and 60B and the body-side facing layers 201. The gap length may generally be greater than 0 mm and less than about 10 mm.

The chassis structure detailed in the embodiment of FIGS. 4A and 4B may be particularly useful where the absorbent insert 50 includes a non-woven material as an outer-layer (e.g. a garment facing layer). For example, the liquid impermeable barrier layer 52 may generally comprise a polymer film which may not be relatively soft or otherwise pleasing to the touch. In such embodiments, implementing a leg elastic covering panel 60 as in the embodiment of FIGS. 3A and 3B which spans between the front and rear panels 40, 41 and fully covers the liquid impermeable barrier layer 52 may be desirable in order to provide an outer (garment-facing) layer which is relatively soft and pleasing to the touch (at least more-so than the liquid impermeable barrier layer 52). In the embodiment of FIGS. 4A and 4B, the liquid impermeable barrier layer 52 may comprise a laminate of multiple layers (not shown), of which at least one is a liquid impermeable barrier layer and where an outermost layer (e.g. the garment-facing layer) comprises a relatively soft nonwoven material or the like which is more pleasing to the touch than the liquid impermeable barrier layer 52. In such embodiments, a large leg elastic covering panel 60 which extends between the front and rear panels 40, 41 and which covers the liquid impermeable barrier layer 52 is not needed. Rather, a lower manufacturing cost can be achieved by having two smaller leg elastic covering panels 60A, 60B.

FIGS. 5A and 5B depict yet another exemplary embodiment of the chassis structure of the garment 20 according to aspects of the present disclosure. In this embodiment, the longitudinal lengths 211, 212, and 213 of the layers 201, 202, and 203 are all equal. However, as can be seen in FIG. 5B, the leg elastic members 70, 75 are still disposed adjacent and directly overlapping the body-facing side of the elastomeric layers 203 (as in the embodiments of FIGS. 3A, 3B, 4A, and 4B). In the present embodiment, however, instead of having a separate leg elastic covering panel 60 (or panels 60A and 60B) which covers the leg elastic members 70, 75, the body-side facing layers 201 act to cover the leg elastic members 70, 75. As described above, forming laminate materials which form the front and rear panels 40, 41 during the process of manufacturing the garment 20 allows for variation in the layers 201, 202, and 203 as opposed to employing pre-laminated materials. In the present embodiment, then, the laminate materials which form the front and rear panels 40, 41 may be formed by placing the leg elastic members 70, 75 overlapping and directly adjacent the body-facing side of elastomeric layers 203 and covering all of the leg elastic members 70, 75 and the elastomeric layers with the body-side facing layers 201. This is in contrast to a garment formed using pre-laminated materials, where the leg elastic members 70, 75 would have had to be placed on top of the body-side facing layers 201 (or under the garment-side facing layers 202). Such embodiments would require an additional material, such as a leg elastic covering panel, to cover the leg elastic members 70, 75 thereby resulting in a product having higher manufacturing costs than a garment 20 of the present embodiment.

Figure 6A:
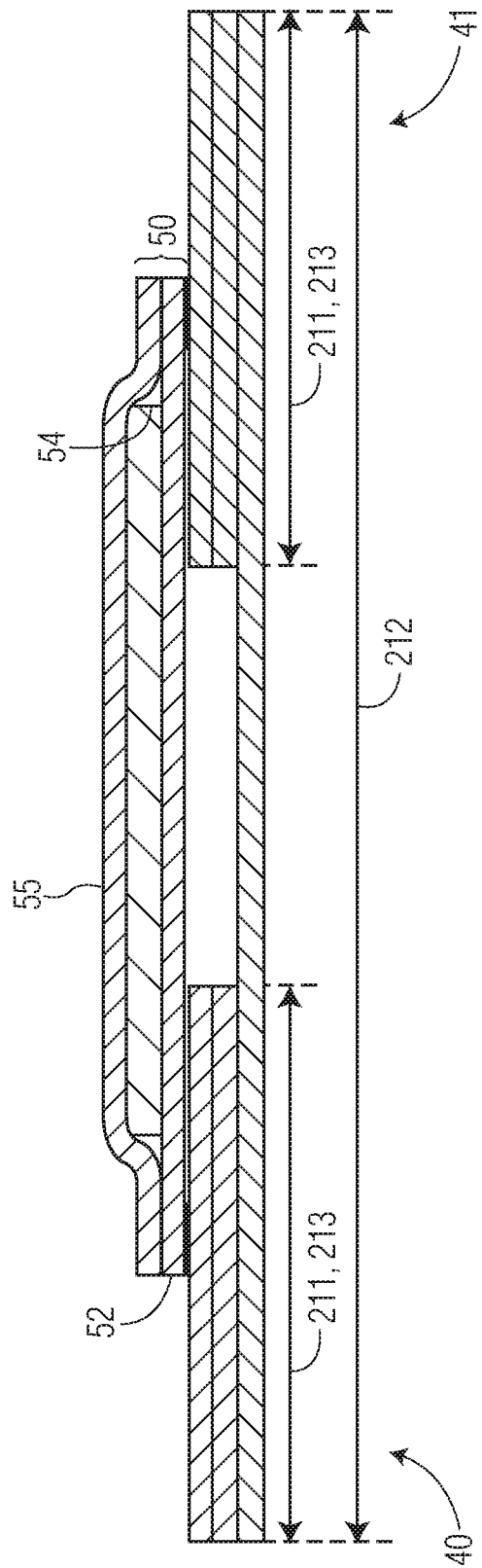
FIG. 6A is another exemplary cross-section view of the article of FIG. 2 as viewed along the line 6-6.
Figure 6B:
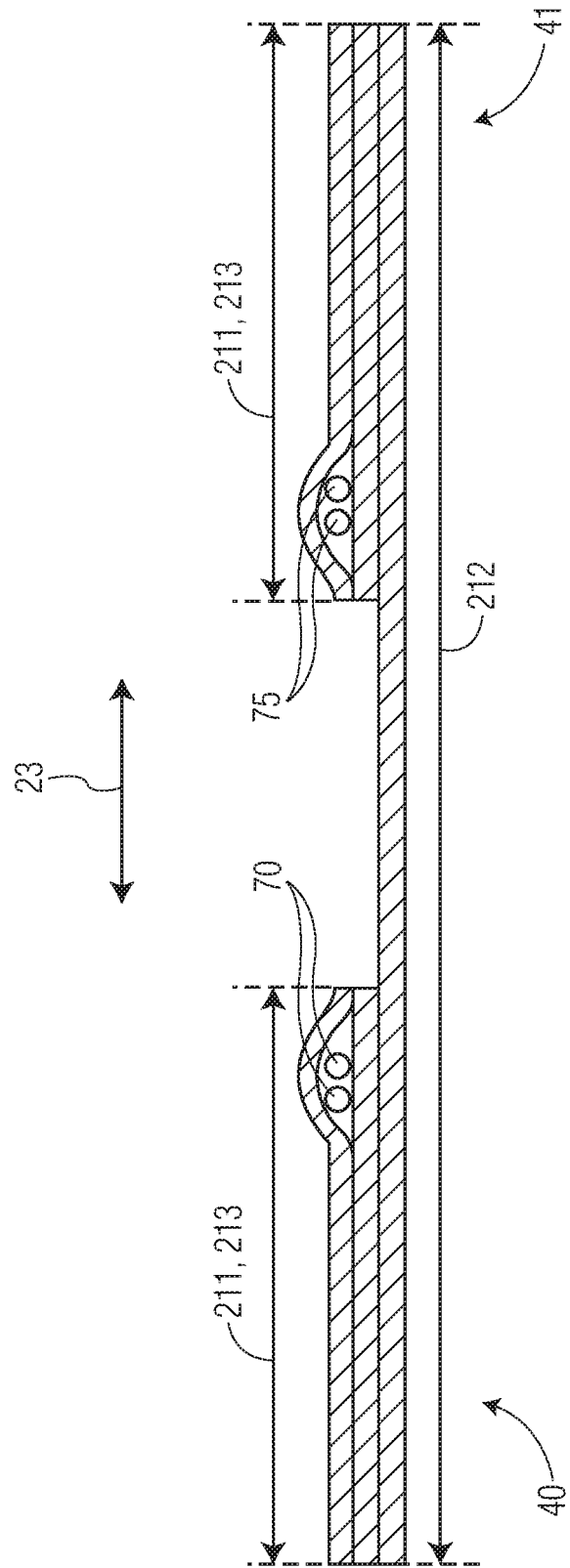
FIG. 6B is another exemplary cross-section view of the article of FIG. 2 as viewed along the line 7-7.

FIGS. 6A, 6B, 7A, and 7B depict further exemplary embodiments of the chassis structure of the garment 20 according to aspects of the present disclosure. In these embodiments, the chassis structure of the garment 20 comprises a "one-piece" construction, with a single layer of material extending between the front and rear panels 40, 41 and comprising a portion of the laminate materials forming each of the panels 40, 41. In the embodiment of FIGS. 6A and 6B it can be seen that there is only a single garment-side facing layer 202 which acts as the garment-side facing layer for both of the front and rear panels 40, 41. Accordingly, the longitudinal length 212 of the garment-side facing layer 202 is greater than the longitudinal lengths 211 and 213 of the body-side facing layers 201 and the elastomeric layers 203. In the embodiment of FIGS. 7A and 7B, it is the body-side facing layer 201 that extends between the front and rear panels 40, 41 and acts as the body-side facing layer 201 for both of the panels 40, 41. Accordingly, the longitudinal length 211 of the body-side facing layer 201 is greater than the longitudinal lengths 212 and 213 of the garment-side facing layers 202 and the elastomeric layers 203.

The embodiments of FIGS. 6A-7B are also similar to the embodiments of FIGS. 5A and 5B, where the leg elastic members 70, 75 are disposed adjacent and directly overlapping the body-facing side of the elastomeric layers 203 with the body-side facing layer(s) 201 covering both of the leg elastic members 70, 75 and the elastomeric layers 203. However, it should be understood that other options for the covering of the leg elastic members 70, 75 of the embodiments of 6A-7B are contemplated. For instance, FIGS. 3A-4B depict embodiments including a leg elastic covering panel 60 (or panels 60A and 60B), which could be employed in any of the embodiments of FIGS. 6A and 6B, with the body-side facing layers 201 disposed such that a portion of each of the elastomeric layers 203 are uncovered by the body-side facing layers 201.

Figure 8A:
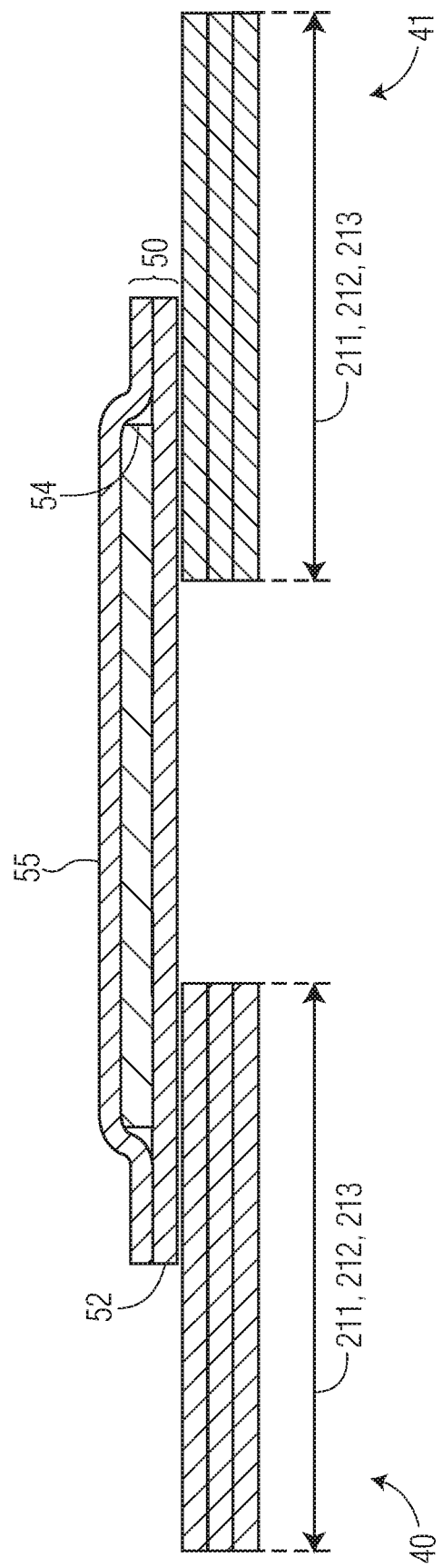
FIG. 8A is another exemplary cross-section view of the article of FIG. 2 as viewed along the line 6-6.

FIGS. 8A and 8B depict another exemplary embodiment of the chassis structure of the garment 20 according to aspects of the present disclosure. However, unlike the previous embodiments which utilize leg elastic members 70, 75 to provide additional elastic support around leg openings 28, the embodiment of FIGS. 8A and 8B utilize the elastomeric layers 203 to provide such elastic support around the leg openings 28. In this embodiment, the elastomeric layers 203 may have longitudinal lengths 213 which are greater than the lengths 211 and/or 212 of the layers 201 and/or 202, as shown in FIG. 8B. In such embodiments, the longitudinal lengths 213 may be equal to the longitudinal length 211 or 212 plus an additional length 215, also as shown in FIG. 8B. The elastomeric layers 203 may further be folded to form in-board facing folds 225. The elastomeric layers 203 may overlap themselves for a distance equal to the additional length 215. This overlapping portion of the elastomeric layers 203 provides the additional elastic support around leg openings 28 that the leg elastic members 70, 75 provide in other embodiments.

In at least some of these embodiments, the elastomeric layers 203 may be shaped such that the longitudinal lengths 213 of the elastomeric layers 203 vary. For example, the elastomeric layers 203 may have longitudinal lengths 213 that are equal to the longitudinal length 211 or 212 along portions of the elastomeric layers 203 which are not proximate the leg openings 28 in a final, wearable configuration of the garment 20, for instance as shown in FIG. 8A. Then, portions of the elastomeric layers 203 which are proximate the leg openings 28 in a final, wearable configuration of the garment 20 may have longitudinal lengths 213 that are greater than the longitudinal lengths 211 and/or 212. For instance, the longitudinal lengths 213 may be equal to the longitudinal length 211 or 212 plus an additional length 215 in order to provide a folded-over portion which provides additional elastic support around the leg openings 28. Of course, it should be understood that there are other ways to produce the folded over portion of the layers 203 rather than by adjusting the longitudinal lengths of the layers 201, 202, and/or 203. Instead, the layers 201, 202, and/or 203 may be offset during production to produce non coterminous edges proximate the central lateral axis 25 to allow for folding over of the elastomeric layers 203 while the longitudinal lengths 211, 212, and/or 213 have different relationships than those described above.

FIGS. 9A and 9B depict still another exemplary embodiment of the chassis structure of the garment 20 according to aspects of the present disclosure. In this embodiment, each of the layers, 201, 202, and 203 of the panels 40, 41 have longitudinal lengths 211, 212, and 213, respectively. Further, the longitudinal lengths 211 and 213 of both the body-side facing layers 201 and the elastomeric layers 203 are less than the longitudinal lengths 212 of the garment-side facing layers 202. This leaves a portion of the garment-side facing layers 202 uncovered on their body-facing side by both the body-side facing layers 201 and the elastomeric layers 203. As shown in FIG. 9B, this leaves room for placement of leg elastic members 70, 75 adjacent and directly overlapping the body-facing side of the portions of the garment-side facing layers 202 that are uncovered by the body-side facing layers 201 and the elastomeric layers 203. This positioning also puts the leg elastic members 70, 75 closer to the central lateral axis 25 than the body-side facing layers 201 and the elastomeric layers 203.

The garment 20 further includes a leg elastic covering panel 60 spanning between the front panel 40 and the rear panel 41 and connected to the liquid impermeable barrier layer 52 of the absorbent insert 50. The leg elastic covering panel 60 further covers both the leg elastic members 70, 75 and at least part of the portions of the garment-side facing layers 202 that are uncovered by both the body-side facing layers 201 and the elastomeric layers 203. The leg elastic covering panel 60 is shown overlapping the body-side facing layers 201 an overlap distance of 221. As described with respect to previous embodiments, the overlap distance 221 may generally be greater than 0 mm and less than about 30 mm, or less than about 25 mm, or less than about 20 mm, or less than about 15 mm, or less than about 10 mm, or less than about 5 mm, thereby covering all of the uncovered portions of the garment-side facing layers 202 and the leg elastic members 70, 75. Although, in other embodiments, the overlap distance 221 may generally be between about 60 mm and about 90 mm.

In other embodiments, however, there may be no overlap between the body-side facing layers 201 and the leg elastic covering panel 60. For example, the leg elastic covering panel 60 may still cover the leg elastic members 70, 75, but there may be a gap having a gap length between the body-side facing layers 201 (and the elastomeric layers 203 in this embodiment) and the leg elastic covering panel 60. This gap distance length (not shown) between the leg elastic covering panel 60 and the layers 201 (and the layers CC) may generally be greater than 0 mm and less than about 10 mm. In such embodiments, then, a portion of the garment-side facing layers 202 may be uncovered by all of the body-side facing layers 201, the elastomeric layers 203, and the leg elastic covering panel 60. However, the absorbent insert 50 may be placed over both of the body-side facing layers 201 and the leg elastic covering panel 60 and may cover the portion of the garment-side facing layers 202 that are left uncovered by the body-side facing layers 201, the elastomeric layers 203, and the leg elastic covering panel 60.

Figure 10A:
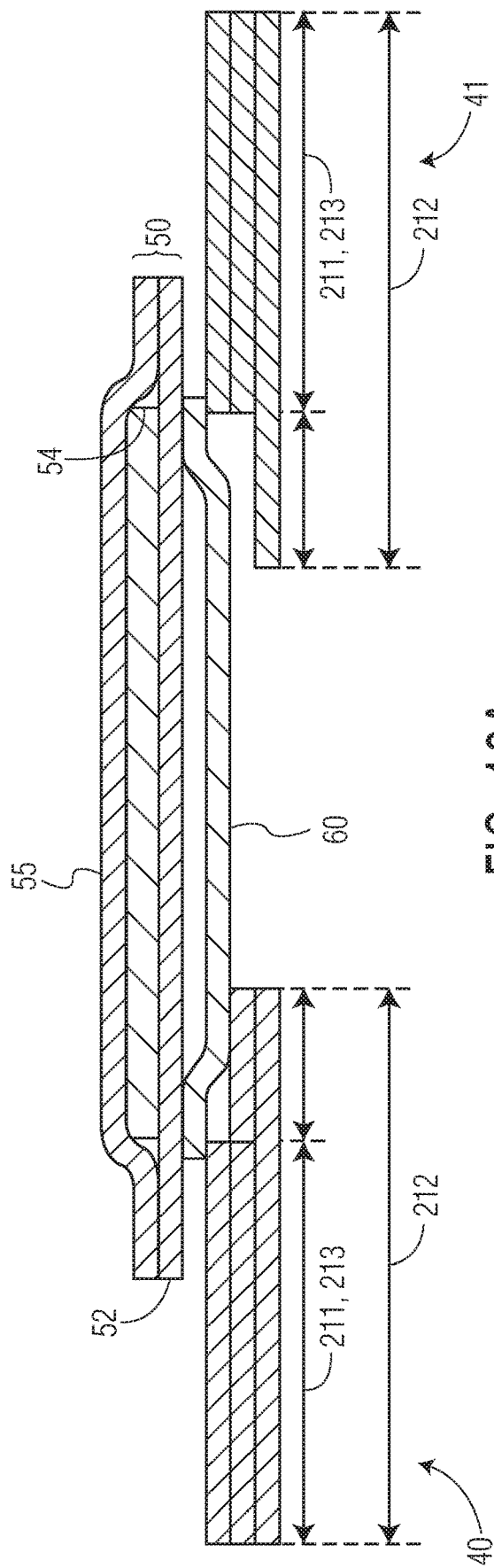
FIG. 10A is another exemplary cross-section view of the article of FIG. 2 as viewed along the line 6-6.

FIGS. 10A and 10B depict a still further exemplary embodiment of the chassis structure of the garment 20 according to aspects of the present disclosure. In all of the previous embodiments, where the leg elastic members 70, 75 are shown as separate members from the layers 201, 202, and 203 of the laminate materials which form the panels 40, 41, the leg elastic members 70, 75 have been shown as elastomeric strands. In the present embodiment of FIGS. 10A and 10B, however, the front leg elastic member 70 may be an elastomeric film material and the rear leg elastic member 75 may comprise one or more elastomeric strands. In the other respects, the embodiment of FIGS. 10A and 10B are the same as the embodiment of FIGS. 9A and 9B. Although, in other embodiments, the front leg elastic member 70 may comprise one or more elastomeric strands while the rear leg elastic member 75 comprises an elastomeric film. It should further be understood that embodiments where the leg elastic members 70, 75 are elastomeric films, or where one of the leg elastic members 70, 75 comprises an elastomeric film while the other of the leg elastic members 70, 75 comprises one or more elastomeric strands, are not limited to the embodiments of FIGS. 10A and 10B. Rather, in any of the above embodiments described herein an elastomeric film material may be substituted for any of the leg elastic members 70, 75 depicted as elastomeric strands, and one or more elastomeric strands may be substituted for any of the leg elastic members 70, 75 depicted as elastomeric films.

Figure 11A:
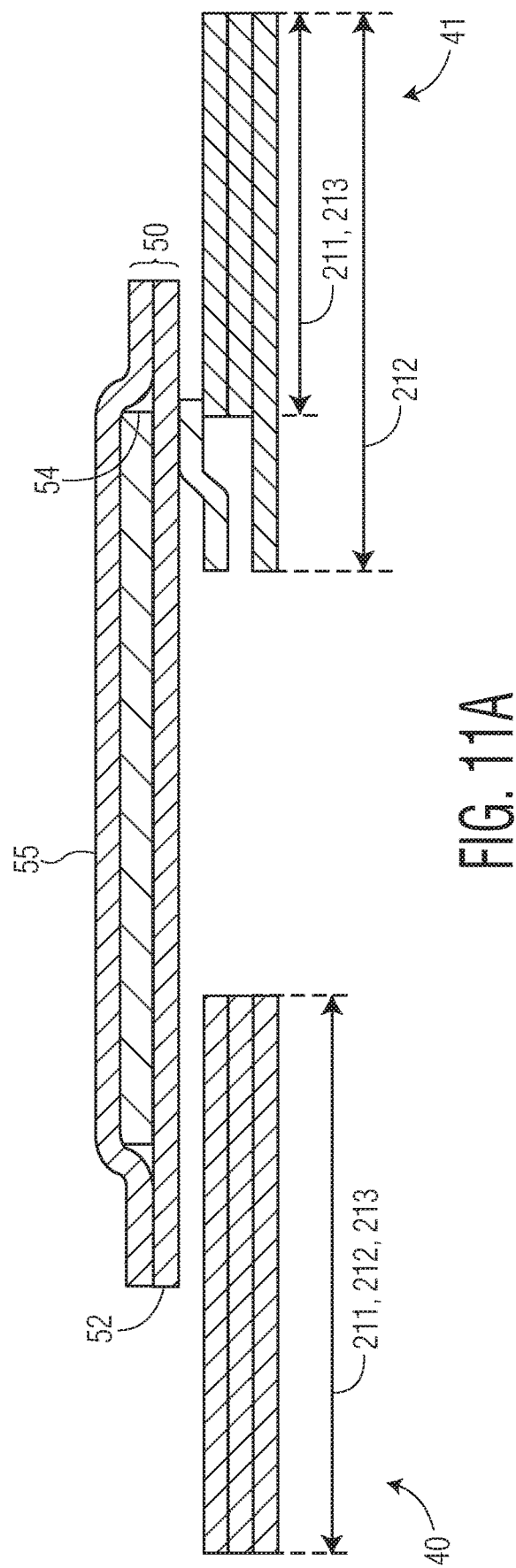
FIG. 11A is another exemplary cross-section view of the article of FIG. 2 as viewed along the line 6-6.

FIGS. 11A and 11B depict an exemplary embodiment of the chassis structure of the garment 20 according to aspects of the present disclosure. The embodiment of FIGS. 11A and 11B is similar to the embodiment of FIGS. 4A and 4B. However, the present embodiment of FIGS. 11A and 11B only includes a rear leg elastic member 75. In such an embodiment, an included leg elastic covering panel 60 may then not span between the front and rear panels 40, 41 (as in the embodiment of FIGS. 4A and 4B) and may be disposed solely in the rear panel 41.

In other exemplary embodiments, however the leg elastic covering panel may still extend between the front and rear panels 40, 41 even where the garment 20 only includes a rear leg elastic member 75. In such embodiments, the front panel 40 may look like that shown in FIG. 11A, with the layers 201, 202, and 203 all having the same longitudinal lengths 211, 212, and 213. However, in other embodiments, the front panel 40 may look similar to those shown in FIG. 4A or 9A, where a portion of the layer 203 or the layer 202 is uncovered by the layer 201. In any of these embodiments, the leg elastic covering panel 60 may overlap and attach to the layer 201 or the layer 202 by an overlap distance similar to any of the distances described above with respect to overlap distance 221.

It should be further understood that, although the other embodiments of the present disclosure, such as those shown in FIGS. 3A-10B, are shown with both front and rear leg elastic members 70, 75, any of these embodiments may alternatively include only a single one of the leg elastic members 70, 75, similar to the embodiments of FIGS. 11A and 11B. The present disclosure contemplates alternative embodiments to any of the described embodiments (including the embodiments of FIGS. 11A and 11B) which include only the rear leg elastic member 75 or the front leg elastic member 70. In such alternative embodiments, the structure of the layers of the laminate materials forming the front and rear panels 40, 41 (and any leg elastic covering panel 60 or panels 60A, 60B) and their relation to each other remains the same as described in the main embodiments.

Other aspects of the present disclosure are directed toward integral waistbands (e.g. waistbands formed from the layers of the front and rear panel, as opposed to attaching wholly separate waistband structures) that garments 20 may include. For instance, in a continuous manufacturing process for forming garments 20 where the laminate materials of the front and rear panels 40, 41 are formed as part of the process, the individual layers of the laminate materials, e.g. layers 201, 202, and 203, may form a waistband. This is in contrast to processes which used pre-laminated materials, where a waistband component may need to be added to the pre-laminated materials which form the front and rear panels 40, 41, or the entire laminate is folded to form a waistband thereby limiting the specific structure of such integral waistbands.

FIGS. 12-17 are cross-sections depicting exemplary waistband structures which may be formed from the layers 201, 202, and 203 which form the front and rear panels 40, 41. For instance, the FIGS. 12-17 may represent cross-sections of just the rear waistband 81 of the garment 20 of FIG. 2 as viewed along a portion of the line 7-7. Any of the described integral waistbands 81 may be combined with any of the embodiments of the present disclosure related to FIGS. 3A-11B. Although only rear waistbands 81 are shown, front waistbands 80 are also contemplated and such structures may be similar to the structures shown with respect to FIGS. 12-17 except mirrored about a longitudinal axis in relation to the structures depicted in FIGS. 12-17. Additionally, the present disclosure contemplates embodiments where the front waistband 80 and the rear waistband 81 differ in structure. Accordingly, embodiments of the present disclosure may employ any one of the described rear waistbands 81 in FIGS. 12-17 as a rear or front waistband 80, 81 and any other of the described rear waistbands 81 as the other waistband 80 or 81.

Figure 12:
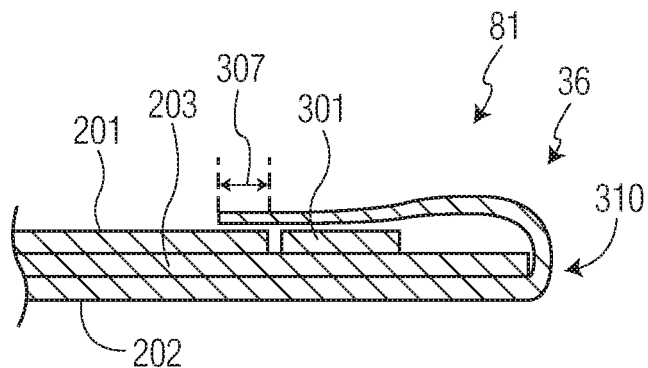
FIG. 12 is an exemplary cross-section depicting a rear waistband of the article of FIG. 2 as viewed along a portion of the line 7-7.

FIG. 12 is a cross-section of the rear waist panel 41 including the rear waist end edge 36 forming an exemplary embodiment of rear waistband 81. In this embodiment, a portion of the elastomeric layer 203 may be uncovered by the body-side facing layer 201 proximate the rear waist end edge 36. A secondary elastic member 301 may be positioned adjacent and directly overlapping the body-facing side of the portion of the elastomeric layer 203 that is uncovered by the body-side facing layer 201. This positioning also puts the secondary elastic member 301 closer to rear waist end edge 36 than the body-side facing layer 201. The secondary elastic member 301 may be an elastomeric film in some embodiments, or may comprise one or more elastomeric strands in other embodiments. The inclusion of the secondary elastic member 301 provides for additional elastic support at the rear waist end edge 36 of the garment 20.

The garment-side facing layer 202, which extends further toward the rear waist end edge 36 than either of the layers 201, 203 may be folded back over all of the secondary elastic member 301, the elastomeric layer 203, and the body-side facing layer 201 forming fold 310. Folding the garment-side facing layer 202 in this manner forms a four-layer laminate structure for the rear waistband 81. The garment-side facing layer 202 may overlap the body-side facing layer 201 by an overlap distance 307 that may be greater than 0 mm and less than about 30 mm, or less than about 25 mm, or less than about 20 mm, or less than about 15 mm, or less than about 10 mm, or less than about 5 mm.

Figure 13:
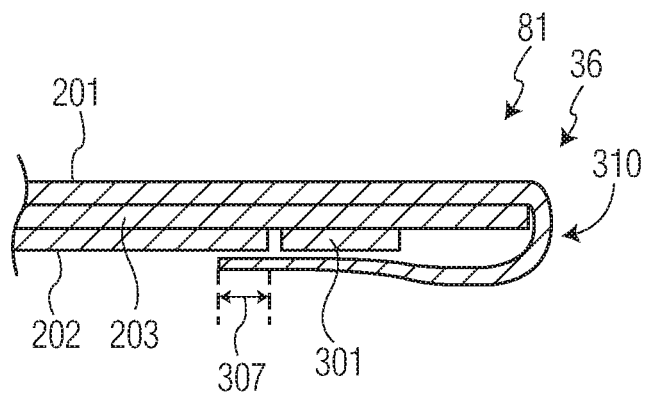
FIG. 13 is another exemplary cross-section depicting a rear waistband of the article of FIG. 2 as viewed along a portion of the line 7-7.

The embodiment of FIG. 13 is similar to the embodiment of FIG. 12, except mirrored. For instance, instead of the elastomeric layer 203 being uncovered by the body-side facing layer 201, the elastomeric layer 203 is uncovered by the garment-side facing layer 202. Then, the secondary elastic member 301 is disposed adjacent and directly overlapping the garment-facing side of the elastomeric layer 203 that are uncovered by the garment-side facing layer 202. This positioning puts the I secondary elastic member 301 closer to the rear waist end edge 36 than the garment-side facing layer 202. Additionally, in this embodiment it is the body-side facing layer 201 that extends further toward the rear waist end edge 36 than either of the layers 202, 203 and that is folded back over all of the secondary elastic member 301, elastomeric layer 203, and the garment-side facing layer 202 forming fold 310.

Figure 14:
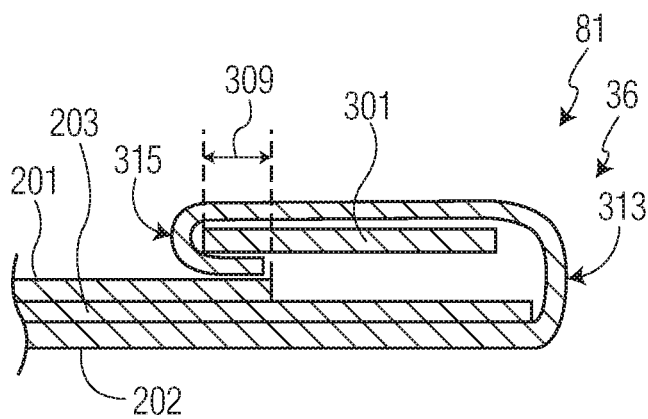
FIG. 14 is another exemplary cross-section depicting a rear waistband of the article of FIG. 2 as viewed along a portion of the line 7-7.

FIG. 14 is a cross-section of the rear waist panel 41 including the rear waist end edge 36 forming another exemplary embodiment of rear waistband 81. Similar to the embodiment of FIG. 12, a portion of the elastomeric layer 203 proximate the rear waist end edge 36 may be uncovered by the body-side facing layer 201. Additionally, a secondary elastic member 301 may be disposed adjacent this uncovered portion of the elastomeric layer 203 and proximate the body-side facing layer 201. However, unlike the embodiment of FIG. 12, the secondary elastic member 301 may directly overlap both of the body-side facing layer 201 and the elastomeric layer 203. In particular, the secondary elastic member 301 may overlap the body-side facing layer 201 by an overlap distance 309. This overlap distance 309 may be generally greater than 0 mm and less than about 30 mm, or less than about 25 mm, or less than about 20 mm, or less than about 15 mm, or less than about 10 mm, or less than about 5 mm. Additionally, the garment-side facing layer 202 may be folded to form both a primary fold 313 and a secondary fold 315, with a portion of the garment-side facing layer 202 disposed between the secondary elastic member 301 and the body-side facing layer 201. Such embodiments form a five-layer laminate structure for the rear waistband 81.

Figure 15:
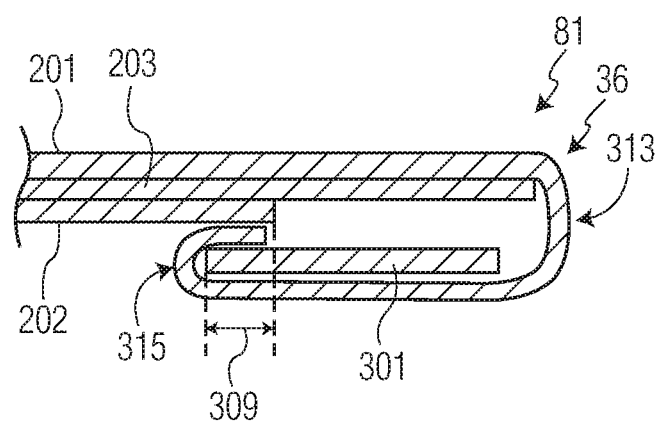
FIG. 15 is another exemplary cross-section depicting a rear waistband of the article of FIG. 2 as viewed along a portion of the line 7-7.

The embodiment of FIG. 15 is similar to the embodiment of FIG. 14, except mirrored. For instance, instead of the elastomeric layer 203 being uncovered by the body-side facing layer 201, the elastomeric layer 203 is uncovered by the garment-side facing layer 202. Then, the secondary elastic member 301 is disposed adjacent this uncovered portion of the elastomeric layer 203 and proximate the garment-side facing layer 202. Additionally, it is the body-side facing layer 201 that is folded to form both a primary fold 313 and a secondary fold 315, with a portion of the body-side facing layer 201 disposed between the secondary elastic member 301 and the garment-side facing layer 202.

Figure 16:
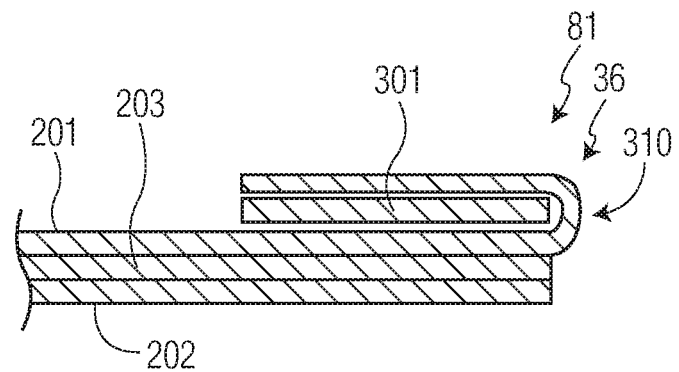
FIG. 16 is another exemplary cross-section depicting a rear waistband of the article of FIG. 2 as viewed along a portion of the line 7-7.
Figure 17:
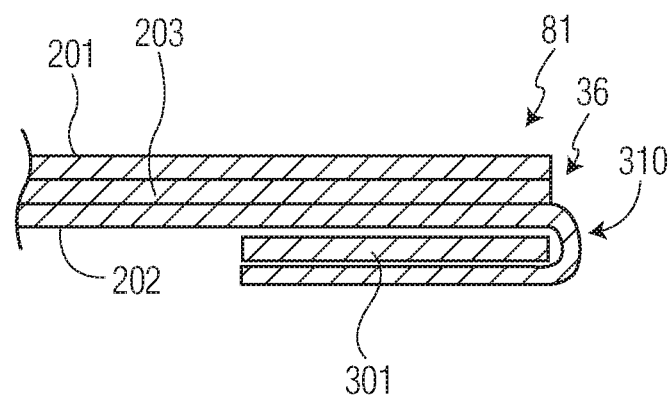
FIG. 17 is another exemplary cross-section depicting a rear waistband of the article of FIG. 2 as viewed along a portion of the line 7-7.

FIGS. 16 and 17 represent yet further embodiments of exemplary rear waistbands 81. In the embodiment of FIG. 16, no portion of the elastomeric layer 203 is uncovered by the body-side facing layer 201. Rather, all of the body-side facing layer 201, the garment-side facing layer 202, and the elastomeric layer 203 form part of the rear waist end edge 36. In the embodiment of FIG. 16, the secondary elastic member 301 is disposed directly adjacent and completely overlapping the body-side facing layer 201. Additionally, the body-side facing layer 201 may be folded over the secondary elastic member 301 forming fold 310. In at least some embodiments, the body-side facing layer 201 may completely cover the secondary elastic member 301.

The embodiment of FIG. 17 is similar to the embodiment of FIG. 16, except mirrored. For instance, the secondary elastic member 301 is disposed directly adjacent and completely overlapping the garment-side facing layer 202. Additionally, it is the garment-side facing layer 202 that may be folded over the secondary elastic member 301 forming fold 310. In at least some embodiments, the garment-side facing layer 202 may completely cover the secondary elastic member 301. The embodiments of FIGS. 16 and 17 may all form 5-layer laminate structures.

Further alternative embodiments to those shown in FIGS. 16 and 17 may have the opposite layer opposite the secondary elastic member 301 folded over the secondary elastic member 301 and the other of the body-side facing layer 201 and the garment-side facing layer 202. For example, in alternative embodiments to those shown in FIG. 16, the garment-side facing layer 202 may be folded over the secondary elastic member 301 (and the elastomeric layer 203 and the body-side facing layer 201). Likewise, in alternative embodiments to those shown in FIG. 17, the body-side facing layer 201 may be folded over the secondary elastic member 301 (and the elastomeric layer 203 and the garment-side facing layer 202). In still further embodiments, the layer which is folded over the secondary elastic member 301 may further comprise a secondary fold to dispose a portion of the layer between the secondary elastic member 301 and the layer which the secondary elastic member 301 directly overlaps. Such a configuration may look similar to FIGS. 14 and 15, except that the elastomeric layer 203 may not be uncovered the body-side facing layer 201 or the garment-side facing layer 202 (e.g. the secondary elastic member 301 would fully overlap the layer to which the secondary elastic member 301 is adjacent).

What is claimed is:

1. A pant-like disposable absorbent garment extending in a longitudinal direction and a lateral direction and having a central longitudinal axis and a central lateral axis, the garment having a front region defining a front waist end edge, a rear region defining a rear waist end edge, and a crotch region longitudinally between the front and rear regions, the crotch region defining two laterally opposed crotch side edges, and the garment defining a garment length extending from the front waist end edge to the rear waist end edge, the garment comprising:
   a front waist panel disposed in the front region comprising:
      a front panel garment-side facing layer,
      a front panel body-side facing layer, and
      one or more front panel chassis elastic members disposed between the front panel garment-side facing layer and the front panel body-side facing layer;
   a rear waist panel disposed in the rear region comprising:
      a rear panel garment-side facing layer,
      a rear panel body-side facing layer,
      one or more rear panel chassis elastic members disposed between the rear panel garment-side facing layer and the rear panel body-side facing layer;
   one or more rear panel leg elastic members directly adjacent in contact with and overlapping the one or more rear panel chassis elastic members in a vertical direction perpendicular to longitudinal and lateral directions; and
   an absorbent assembly disposed between the front panel and the rear panel, the absorbent assembly comprising a topsheet, a backsheet, and an absorbent body disposed between the topsheet and the backsheet.

2. The garment of claim 1, wherein the one or more rear panel leg elastic members are disposed adjacent a body-side surface of the one or more rear panel chassis elastic members.

3. The garment of claim 2, wherein the rear panel body-side facing layer fully covers the one or more rear panel leg elastic members.

4. The garment of claim 3, wherein the rear panel body-side facing layer extends between the rear panel and the front panel and forms both the rear panel body-side facing layer and the front panel body-side facing layer.

5. The garment of claim 3, wherein the front panel body-side facing layer extends between the front panel and the rear panel and forms both the front panel body-side facing layer and the rear panel body-side facing layer.

6. The garment of claim 2, wherein the one or more rear panel leg elastic members and at least a portion of the one or more rear panel chassis elastic members are uncovered by the rear panel body-side facing layer, and wherein the garment further comprises a leg elastic covering panel which covers the one or more rear panel leg elastic members.

7. The garment of claim 6, wherein the leg elastic covering panel further covers at least a portion of the one or more rear panel chassis elastic members which are uncovered by the rear panel body-side facing layer.

8. The garment of claim 6, wherein the leg elastic covering panel overlaps the rear panel body-side facing layer by an overlap distance that is greater than 0mm and less than about 15 mm.

9. The garment of claim 6, wherein at least a portion of the one or more front panel chassis elastic members are uncovered by the front panel body-side facing layer, and the leg elastic covering panel extends between the rear panel and the front panel and covers at least a portion of the one or more front panel chassis elastic members which are uncovered by the front panel body-side facing layer.

10. The garment of claim 1, wherein the one or more front panel chassis elastic members comprises a plurality of elastomeric strands, and wherein the one or more rear panel chassis elastic members comprise an elastomeric film.

11. The garment of claim 1, further comprising one or more front panel leg elastic members, and wherein the one or more front panel leg elastic members comprise an elastomeric film and the one or more rear panel leg elastic members comprise a plurality of elastomeric strands.

12. A pant-like disposable absorbent garment extending in a longitudinal direction and a lateral direction and having a central longitudinal axis and a central lateral axis, the garment having a front region defining a front waist end edge, a rear region defining a rear waist end edge, and a crotch region longitudinally between the front and rear regions, the crotch region defining two laterally opposed crotch side edges, and the garment defining a garment length extending from the front waist end edge to the rear waist end edge, the garment comprising:
   a front waist panel disposed in the front region comprising:
      a front panel garment-side facing layer,
      a front panel body-side facing layer,
      one or more front panel chassis elastic members disposed between the front panel garment-side facing layer and the front panel body-side facing layer, wherein at least a portion of the one or more front panel chassis elastic members are uncovered by the front panel body-side facing layer, and
      one or more front panel leg elastic members directly adjacent in contact with and overlapping a body-facing side of the one or more front panel chassis elastic members in a vertical direction perpendicular to longitudinal and lateral directions;

a rear waist panel disposed in the rear region comprising:
  a rear panel garment-side facing layer,
  a rear panel body-side facing layer,
  one or more rear panel chassis elastic members disposed between the rear panel garment-side facing layer and the rear panel body-side facing layer, wherein at least a portion of the one or more rear panel chassis elastic members are uncovered by the rear panel body-side facing layer, and
  one or more rear panel leg elastic members directly adjacent in contact with and overlapping a body-facing side of the one or more rear panel chassis elastic members in a vertical direction perpendicular to longitudinal and lateral directions;

a leg elastic covering panel extending between the front panel and the rear panel, the leg elastic covering panel:
  covering the one or more front panel leg elastic members and overlapping the front panel body-side facing layer by an overlap distance that is greater than 0 mm and less than about 15 mm, and
  covering the one or more rear panel leg elastic members and overlapping the rear panel body-side facing layer by an overlap distance that is greater than 0 mm and less than about 15 mm; and an absorbent assembly disposed between the front panel and the rear panel, the absorbent assembly comprising a topsheet, a backsheet, and an absorbent body disposed between the topsheet and the backsheet.

13. The garment of claim 12, wherein the one or more front panel chassis elastic members comprises a plurality of elastomeric strands, and wherein the one or more rear panel chassis elastic members comprise an elastomeric film.

* * * * *